(12) United States Patent
Hartman et al.

(10) Patent No.: US 11,385,215 B2
(45) Date of Patent: Jul. 12, 2022

(54) SOIL HEALTH INDICATORS USING MICROBIAL FUNCTIONAL GENES

(71) Applicant: Trace Genomics, Inc., Burlingame, CA (US)

(72) Inventors: Wyatt Hugh Hartman, San Francisco, CA (US); David Curtis Stone, San Francisco, CA (US); Ariel David Zajdband, Berkeley, CA (US); Poornima Parameswaran, Menlo Park, CA (US); Di Wu, San Francisco, CA (US); Deepak Chandran, Walnut Creek, CA (US)

(73) Assignee: Trace Genomics, Inc., Redwood City, CA (US)

( * ) Notice: Subject to any disclaimer, the term of this patent is extended or adjusted under 35 U.S.C. 154(b) by 0 days.

(21) Appl. No.: 16/799,823

(22) Filed: Feb. 24, 2020

(65) Prior Publication Data

US 2020/0271636 A1 Aug. 27, 2020

Related U.S. Application Data

(60) Provisional application No. 62/810,338, filed on Feb. 25, 2019.

(51) Int. Cl.
| | | |
|---|---|---|
| *G01N 33/24* | (2006.01) | |
| *C12N 15/10* | (2006.01) | |
| *G06F 16/29* | (2019.01) | |
| *G16B 20/00* | (2019.01) | |

(52) U.S. Cl.
CPC ......... *G01N 33/24* (2013.01); *C12N 15/1003* (2013.01); *G06F 16/29* (2019.01); *G16B 20/00* (2019.02); *G01N 2033/243* (2013.01); *G01N 2033/245* (2013.01)

(58) Field of Classification Search
CPC ........ G01N 33/24; G06F 16/29; G16B 20/00; C12N 15/1003
See application file for complete search history.

(56) References Cited

U.S. PATENT DOCUMENTS

| | | |
|---|---|---|
| 7,255,989 B1 | 8/2007 | Jeannin et al. |
| 2016/0232621 A1* | 8/2016 | Ethington .............. G06Q 50/02 |
| 2018/0148778 A1 | 5/2018 | Mercer |
| 2020/0024636 A1* | 1/2020 | Claypool et al. ........ C12Q 1/64 |

OTHER PUBLICATIONS

Nielsen et al., Microorganisms as indicators of soil health, 2002, NERI Technical Report, 388, p. 1-85 (Year: 2002).*
Vestergaard et al., Making big data smart—how to use metagenomics to understand soil quality, 2017, Biol Fertil Soils, 53, p. 479-A84 (Year: 2017).*
Meneghine et al., Metagenomic analysis of soil and freshwater from zoo agricultural area with organic fertilization, 2017, PLOS one, p. 1-20 (Year: 2017).*
Shokralla et al., 2012, Next-generation sequencing technologies for environmental DNA research, 2012, 21, p. 1794-1805 (Year: 2012).*
Jeffries et al., Metagenomic Functional Potential Predicts Degradation Rates of a Model Organophosphorus Xenobiotic in Pesticide Contaminated Soils, 2018, frontiers in Microbiology, 9(147), p. 1-12 (Year: 2018).*
An et al., Statistical Approach of Functional Profiling for a Microbial Community, 2014, PLOS ONE, 9(9), p. 1-11 (Year: 2014).*
Srinvasulu, Enzymes and Pesticides, 2014, OMICS Group, p. 1-10 (Year: 2014).*
Young et al. 2014, Limitations and recommendations for successful DNA extraction from forensic soil samples: A review, 2014, Science and Justice, 2014, p. 238-244 (Year: 2014).*
Rinot et al., Soil health assessment: A critical review of current methodologies and a proposed new approach, 2019, Science of the Total Environment, p. 1484-1491 (Year: 2019).*
PCT Invitation to Pay Additional Fees and, Where Applicable, Protest Fee, PCT Application No. PCT/US2020/19634, dated Apr. 14, 2020, 2 pages.
Kuske, C. R et al., "Diverse Uncultivated Bacterial Groups from Soils of the Arid Southwestern United States That are Present in Many Geographic Regions," Applied and Environmental Microbiology, Sep. 1997, pp. 3614-3621, vol. 63, No. 9, [Online] [Retrieved on Aug. 5, 2020], Retrieved from the Internet<URL: https://aem.asm.org/content/aem/63/9/3614.full.pdf>.
PCT International Search Report and Written Opinion, PCT Application No. PCT/US2020/019634, dated Jun. 15, 2020, 14 pages.
Sanger, F. et al., "DNA sequencing with chain-terminating inhibitors," PNAS, 1977, vol. 72, No. 12, pp. 5463-5467.

* cited by examiner

*Primary Examiner* — Olivia M. Wise
*Assistant Examiner* — Kaitlyn L Minchella
(74) *Attorney, Agent, or Firm* — Fenwick & West LLP

(57) ABSTRACT

In various embodiments, an analytics system determines nucleic acid sequence reads of genetic material in a soil sample from a geographical location. The analytics system determines a first set of measures of a plurality of gene functions represented in the nucleic acid sequence reads. The analytics system determines a second set of measures of a plurality of metabolic pathways of microorganisms present in soil at the geographical location. The analytics system determines a third set of measures of a plurality of soil health indicators of the soil at the geographical location, the plurality of soil health indicators including a plurality of levels of granularity. The analytics system determines a measure of an agronomic attribute of the soil at the geographical location as a function of the first, second, and third sets of measures.

16 Claims, 9 Drawing Sheets

800

```
Determine nucleic acid sequence reads of genetic
material in a soil sample from a geographical location
810
                    │
                    ▼
Determine a first set of measures of gene functions
820
                    │
                    ▼
Determine a second set of measures of metabolic
pathways of microorganisms present in soil at the
geographical location
830
                    │
                    ▼
Determine a third set of measures of soil health
indicators of the soil at the geographical location
840
                    │
                    ▼
Determine a measure of an agronomic attribute of the
soil at the geographical location as a function of the
first, second, and third sets of measures
850
                    │
                    ▼
┌ ─ ─ ─ ─ ─ ─ ─ ─ ─ ─ ─ ─ ─ ─ ─ ─ ─ ─ ─ ─ ─ ─ ─ ┐
│  Treat the soil according to the measure of the  │
│             agronomic attribute                  │
│                    860                           │
└ ─ ─ ─ ─ ─ ─ ─ ─ ─ ─ ─ ─ ─ ─ ─ ─ ─ ─ ─ ─ ─ ─ ─ ┘
```

FIG. 8

SOIL HEALTH INDICATORS USING MICROBIAL FUNCTIONAL GENES

CROSS REFERENCE TO RELATED APPLICATION

This application claims the benefit of priority to U.S. Provisional Application No. 62/810,338, filed on Feb. 25, 2019, which is incorporated herein by reference in its entirety for all purposes.

TECHNICAL FIELD

This disclosure generally relates to soil health indicators, gene functions, and agronomy.

BACKGROUND

The soil microbiome includes thousands of organisms, including bacteria, fungi, nematodes, and insects, among other microbes. These organisms collectively contain tens to hundreds of thousands of unique genes, which encode proteins that form enzymes, which in turn catalyze reactions of microbial metabolic pathways. Metagenomics (also referred to as environmental genomics or community genomics) is the science of describing the profile of microbiomes detected in a biological sample such as soil, here including the functional genes underlying microbial metabolism. As one application, it is desirable to predict whether a farmer's field will produce a high or low crop yield, and whether the crops will develop disease.

Further, it is challenging to determine the impact of microbiome in soil on crop yield and disease pressure. For example, crop yield may be altered by microbial control over nutrient cycling such that added nutrients are lost due to microbial activity. This yield loss may not be a direct function of the abundance of the underlying microbes, but could also arise due to their interactions with other factors in soils. Moreover, in many cases these gene abundances may not directly correspond to the abundances of known, named organisms.

BRIEF DESCRIPTION OF THE FIGURES

The disclosed embodiments have advantages and features which will be more readily apparent from the detailed description, the appended claims, and the accompanying figures (or drawings). A brief introduction of the figures is below.

FIG. 8 illustrates an example process for determining a measure of an agronomic attribute according to an embodiment.

SUMMARY

Figure 1:
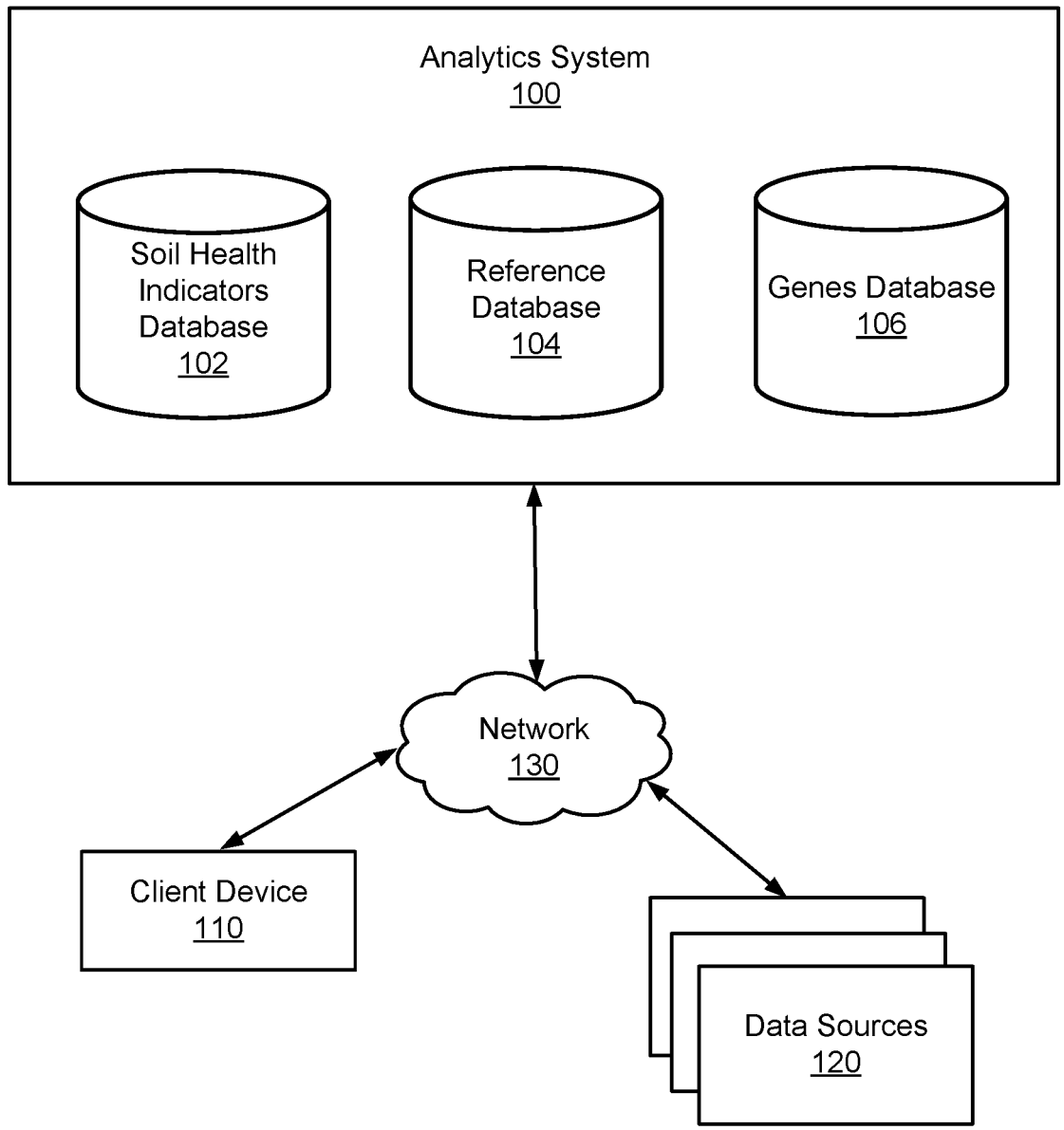
FIG. 1 illustrates an example system environment for an analytics system according to an embodiment.

An analytics system uses soil health indicators to determine metrics for soil samples, for example, indicating performance of crops grown in geographical locations having the soil samples.

In various embodiments, a method includes determining nucleic acid sequence reads of genetic material in a soil sample from a geographical location. The method further includes determining, by processing the nucleic acid sequence reads, a first set of measures of a plurality of gene functions represented in the nucleic acid sequence reads. The method further includes determining, by processing the plurality of gene functions, a second set of measures of a plurality of metabolic pathways of microorganisms present in soil at the geographical location. The method further includes determining, by processing the plurality of metabolic pathways, a third set of measures of a plurality of soil health indicators of the soil at the geographical location, the plurality of soil health indicators including a plurality of levels of granularity. The method further includes determining a measure of an agronomic attribute of the soil at the geographical location as a function of the first, second, and third sets of measures. In some embodiments, the measure of an agronomic attribute of the soil is transmitted to a client device for display.

In an embodiment, determining the second set of measures of the plurality of metabolic pathways of microorganisms comprises determining a function of measures of constituent genes from the plurality of gene functions. In an embodiment, determining the third set of measures of the plurality of soil health indicators comprises determining a function of the plurality of metabolic pathways corresponding to the nucleic acid sequence reads.

In an embodiment, the plurality of gene functions includes one or more of: nitrogen cycling, phosphorous cycling, carbon cycling, or oxygen availability. In an embodiment, the agronomic attribute is nitrogen mineralization and the plurality of metabolic pathways includes at least secreted proteases and urea mineralization.

In an embodiment, the method further includes determining a recommendation for treatment of the soil at the geographical location using at least the measure of the agronomic attribute. In an embodiment, the method further includes filtering out at least one metabolic pathway of the plurality of metabolic pathways.

In an embodiment, the plurality of levels of granularity includes a level closer to biological attributes and another level closer to agronomic attributes.

In various embodiments, a method includes receiving metadata describing a soil sample, where the metadata indicates one or more types of crops grown in a geographical location having the soil sample. The method further includes determining nucleic acid sequence reads of the soil sample. The method further includes determining, for each nucleic acid sequence read of at least a subset of the nucleic acid sequence reads, functional descriptors of the genes represented in nucleic acid sequence reads. The method further includes determining reference metrics of soil samples from geographical locations in which the one or more types of crops were grown. The method further includes determining a metric of the soil sample using the functional descriptors and the reference metrics. The method further includes transmitting the metric to a client device for display on a user interface.

In an embodiment, determining the metric of the soil sample comprises determining a value of a soil health indicator of the soil sample using the functional descriptors. The method further includes determining a distribution of values of the soil health indicator for the soil samples using the reference metrics. The method further includes determining a percentile of the value with respect to the distribution of values.

In an embodiment, determining the functional descriptors comprises determining a plurality of microbial functional genes (also referred to herein as functional genes or microbial genes) in the soil sample. The method further includes determining, for each of the plurality of genes, a count of the genes in the soil sample. The method further includes normalizing these counts using a total count of genes in the soil sample or by other methods such as single copy marker genes, sequence read depth, etc.

In an embodiment, determining the nucleic acid sequence reads of the soil sample comprises extracting microbial material from the soil sample. The method further includes generating nucleic acid sequence reads of the microbial material. The method further includes filtering the nucleic acid sequence reads by read quality scores.

In various embodiments, a method includes obtaining a soil sample from a geographical location. The method further includes receiving metadata indicating the geographical location. The method further includes determining a plurality of functional genes in the soil sample. The method further includes determining, for each of the plurality of functional genes, a measure of the functional gene in the soil sample. The method further includes determining functional descriptors of genes represented in the soil sample using the measures of the functional genes. The method further includes determining reference metrics of soil samples from geographical locations within a threshold distance of the geographical location. The method further includes determining a metric of the soil sample using the functional descriptors and the reference metrics. The method further includes transmitting the metric to a client device for display on a user interface.

In various embodiments, one or more processors may execute instructions stored by a non-transitory computer-readable storage medium to control a computer system to perform steps of any of the above methods. In various embodiments, a system includes a sampling tube for obtaining a soil sample from a geographical location. The system further includes one or more processors and a memory, the memory storing computer program instructions that when executed by the one or more processors cause the one or more processors to perform steps of any of the above methods.

DETAILED DESCRIPTION

I. Example System Overview

FIG. 1 illustrates an example system environment for an analytics system 100 according to an embodiment. The system environment shown in FIG. 1 includes the analytics system 100, a client device 110, and one or more data sources 120, which are connected to each other via a network 130 (e.g., the Internet). In other embodiments, different or additional entities can be included in the system environment. For instance, the system environment may include laboratory equipment to process samples and generate nucleic acid sequence reads of samples. In some embodiments, the nucleic acid sequence reads are deoxyribonucleic acid (DNA) sequences or fragments, which may have varying lengths of base pairs. In other embodiments, the nucleic acid sequence reads are ribonucleic acid (RNA) sequences or fragments, also having varying lengths of base pairs. The analytics system 100 can process any number of nucleic acid sequence reads generated by processing a soil sample, where the nucleic acid sequence reads are indicative of genetic material in the soil sample. The genetic material can originate from microbes or other sources such as other organisms, biological waste, and plants, among other matter present in a soil sample. Though only one client device 110 is shown in FIG. 1, the system environment may include additional client devices 110. The functions performed by the various entities of FIG. 1 may vary in different embodiments.

The analytics system 100 determines metrics of soil samples using soil health indicators. A soil health indicator is defined as a value of microbial driven function pertinent to agricultural production. A soil health indicator may reflect soil mineral and organic element availability, plant growth promoting factors, interaction with plant pathogens, crop performance, or other indicators of soil function or health. A soil health indicator may be derived by processing nucleic acids of a soil sample, for example, by sequencing deoxyribonucleic acid (DNA) or ribonucleic acid (RNA) to determine functional descriptors associated with microbes (also referred to herein as microorganisms or organisms) present in the soil sample. Soil health indicators may be used to predict physical attributes of crops (e.g., stem size, plant height, or fruit size), crop yield, or cycling of mineral and organic elements in soils including nutrients, carbon, and oxygen.

The analytics system 100 obtains or receives soil samples from users (e.g., of the analytics system 100) such as farmers or other third parties (e.g., agriculture-related companies). In some embodiments, the analytics system 100 or an entity associated with the analytics system 100 provides a sampling tube 280 to a user, e.g., as part of a kit for collection of soil sample or related information. The user collects a soil sample using the sampling tube 280 and returns the sampling tube 280 (e.g., via mail or other delivery methods) to the analytics system 100 for processing. An interior of the sampling tube 280 may be sterilized and may include a preservative solution, for example, to help maintain conditions of the soil sample or microbes present in the soil sample. The analytics system 100 may determine or indicate to a user a target volume, mass, or weight, of the soil sample to be collected using the sampling tube 280. The analytics system 100 may also provide sampling recommendations or protocols to users. For example, the sampling recommendations indicate a range of depth for soil collection (e.g., 0-6 inches below ground level), which may vary based on type of crop, geographical location, or other factors. This range of depth instructs the user how to conduct the sampling of the soil, including to what depth the sample should be extracted in a particular region in California for a specific type of crop (e.g., corn or a particular varietal of corn).

In some embodiments, the sampling tubes 280 are associated with a label (e.g., barcode or QR code) for tracking or identification. The analytics system 100 associates information describing users or soil samples with identification keys of obtained soil samples. For example, a soil sample is identified with an agricultural field, geographical location, or one or more types of crops. The information may include metadata, which is further described below with reference to FIG. 2A. The analytics system 100 may receive the information describing users or soil samples from client devices 110 of users, e.g., before, after, or along with receiving soil samples from users. The analytics system 100 may also receive the information from other forms of delivery such as a physically delivered document or device (e.g., mailed or provided in-person). By using the identification keys and associated information, the analytics system 100 distinguishes between multiple soil samples from the same user or different users. For instance, a user may provide soil samples from different geographical zones (e.g., geospatial units) of a field or farm, or from geographical zones in which different types of crops are grown. The analytics system 100 may homogenize multiple soil samples into a composite sample representative of a geographical zone. For example, the soil samples are obtained from multiple sampling locations within the geographical zone and then combined into the composite sample to be more representative of the geographical zone as a whole. In an embodiment, the sampling locations may be based on a pattern spread across the geographical zone. A field may be organized into geographical zones using grid cells or other configurations.

The analytics system 100 determines a metric of a soil sample in view of a "crop community," that is, reference information associated with the soil sample. For example, the reference information includes data of other soil samples having similar conditions, in which same types of one or more crops were grown, treated with similar management or agricultural practices, or having other traits in common with the soil sample. In an example use case, a crop community corresponds to soil from a geographical region such as a city, state, or country. The crop community can be further differentiated by crops such as one or more vegetables, fruits, or nuts, among others. The analytics system 100 stores metrics in the soil health indicators database 102.

The analytics system 100 stores reference information in the reference database 104. The analytics system 100 may receive reference information from one or more data sources 120 or client devices 110. For instance, users of the analytics system 100 provide soil samples and information (e.g., metadata) describing the soil samples that the analytics system 100 may use as reference information for other soil samples. The analytics system 100 stores information derived using the soil samples or metadata as reference information in the reference database 104. Moreover, the analytics system 100 may associate reference information with associated metadata such as geographic location, one or more crop types, crop season, or other information describing an agricultural field. Accordingly, the analytics system 100 may perform lookup for reference information by querying the reference database 104 using metadata. For example, the analytics system 100 can lookup reference information for agricultural fields within a certain region or radius of geographical locations.

The analytics system 100 provides metrics to users, e.g., for presentation on a client device 110 of a user. The analytics system 100 may also derive recommendations from metrics regarding agricultural techniques. Based on metrics or recommendations, farmers or other users are informed as to a variety of actions that determine inputs or practices to use on fields, when to plant, where to plant, which crops to plant, or which varietals of those crops to plant, among other insights that may improve crop or soil health or performance.

A client device 110 comprises one or more computing devices capable of processing data as well as transmitting and receiving data over the network 130. For example, a client device 110 may be a desktop computer, a laptop computer, a mobile phone, a tablet computing device, an Internet of Things (IoT) device, or any other device having computing and data communication capabilities. The analytics system 100 may provide information to the client device 110 for presentation to a farmer or another user. The information may include metrics or recommendations determined by the analytics system 100 regarding soil samples or crops.

Though not shown in FIG. 1, the analytics system 100 may include one or more processors for manipulating and processing data, a network connection for communicating with other devices, and a non-transitory computer-readable storage medium for storing data, program code, or program instructions associated with various applications. It is noted that a storage medium may include volatile memory (e.g., random access memory) or non-volatile storage memory such as hard disks, flash memory, and external memory storage devices. The one or more processors may execute instructions to perform steps of one or more processes, e.g., the process described below with reference to FIG. 2A.

For purposes of explanation, this disclosure uses soil samples generally as example use cases, though the embodiments described herein may be adapted for systems and methods using other types of biological samples or physical samples. For instance, the biological sample may be at least in part a liquid or aqueous sample used for growing plants in a hydroponics system. As a different example, the biological sample may be a sample of a gut microbiome of a subject (e.g., a human or another type of organism), and the analytics system 100 may determine metrics associated with physiology or other attributes of the subject.

II. Example Soil Health Indicators

In various embodiments, the analytics system 100 determines functional gene based soil health indicators (SHI) for one or more of Nitrogen cycling, Phosphorus cycling, Soil Carbon availability, and Oxygen availability. Individual indicators for each of these element cycles represent simplified versions of more complex biological transformations, derived from even more detailed lists of metabolic pathways and their constituent genes, present across a large number of microbial organisms with different gene sequence variations. The analytics system 100 determines soil health indicators using curation of multiple data sources for gene sequences, pathways, and element transformations, which may not necessarily be designed for application to soils or agriculture. The curation process may include one or more techniques known to one skilled in the art of genomics, metabolism, biogeochemistry, or agronomy. Techniques may include processes to determine where to obtain data, how to group the data, and how to analyze or distill the data, and how to experimentally validate the data, among others. Moreover, complex biological and chemical cycles may be further distilled into simplified indicators which are interpretable and relevant to agricultural operators using expert judgment, benchmarking, and validation.

In some embodiments, simplified, composite SHI are derived from genes which provide a representation of biological reactions transforming molecules containing each element in soils. Lists of genes involved in these transformations may be obtained and cross validated from multiple sources, many of which may be incomplete sources compared to the collected information. Scientific literature may be used in conjunction with public databases on metabolic pathways or schemes of gene categorization including the MetaCyc database, the Kyoto Encyclopedia of Genes and Genomes (KEGG) and SEED gene ontologies. Further data sources may be used to obtain additional gene annotation sources or models, including the UniProt, Pfam, and InterPro databases. These databases generally represent known molecular biology across organisms as organized for varying purposes which are not commonly organized to represent element cycling, soils, or agriculture.

As a general note, several of the most relevant genes are known to be horizontally transferred among microbes (such that organism names or name hierarchies are not necessarily deterministic of gene count). The number of these gene copies may vary within a given organism name or group (taxonomy). Further, microbial genes affecting plant growth and nutrition may have complex interactions with the soil environment, such that relationships vary by soil types or geographical locations. Methods to derive indicators of soil function (e.g., including gene groupings) may need to account for such interactions and localities during the validation of different indicator formulations or computed derivations.

The below descriptions provide various working examples of soil health indicators and their generation.

A. Processing Gene Lists from Databases

Existing genetic and metabolic databases may have incomplete representation of metabolism in soil, which makes it challenging to map information from these databases to soil functions. Some metabolic databases are organized around cellular metabolism (e.g., human or microbial), and may not map clearly to soil metabolism, including the omission of one or more metabolic functions.

The SEED protein database includes a list of genes that code for enzymes involved in phosphorus cycling. Yet this database is not organized around metabolic pathways and includes several genes without known environmental functions. Examples of such functions may include genes involved in intracellular phosphorus cycling, which may not have bearing on extracellular phosphorus cycling. These extraneous genes may present a false signal in agricultural soils.

The analytics system 100 filters out these extraneous genes from the data underlying soil health indicator calculations. Conversely, once relevant genes for phosphorus cycling are identified, it may become apparent that these genes are indeed present in metabolic databases (e.g. KEGG or Metacyc) and other protein databases (e.g., Pfam or Uniprot), even though the genes may not necessarily be explicitly organized or represented in metabolic maps.

B. Resolving Gene Ambiguity in Genomic Databases

In some embodiments, resulting element cycling gene lists are evaluated for consistency and inclusion among sources. The analytics system 100 may apply further curation to consider genes that might provide ambiguous information as the result of genes being involved in multiple pathways, with reversible reactions, having high sequence identity with similar genes with different functions (homologs), etc.

In some embodiments, from these gene lists, individual SHIs are calculated using hierarchical categorization schemes including both commonly recognized metabolic pathways, and expert curated classification (grouping) schemes, which may include excluding some genes with ambiguous functions in soils. Gene based indicators of soil health may be derived using expert judgment, benchmarking against agricultural data, and other validation processes to deliver simplified but accurate representations of underlying biology and chemistry which are relevant in an agricultural context.

Genomic or metabolic databases present genes as a collection of sequences with similar function or protein structure. These collections of genes may include sequences from organisms in which function differs from an agronomic attribute. For example, the KEGG database organizes genes by KEGG orthology (KO), which is a collection of genes with a similar function. Gene sequences from individual organisms associated with a given KO may be classified with a single identifier. In some embodiments, the analytics system 100 matches unknown DNA sequences from agricultural soils to a gene category or KO.

A given KO may include genes from organisms that perform different functions in the environment. For example, the KO identifier K00370 (and genomic neighbor K00371) are a collection of three similar genes involved in nitrogen cycling with different functions: narG, narZ, and nxrA (or for K00371, narH, narY, and nxrB). Notably, these genes are also represented with a single identifier in the Pfam database, which does not explicitly identify underlying differences in genes or the chemical reactions carried out by them. Reduction of nitrite ($NO_2-$) to nitrate ($NO_3-$) by nitrite oxidizing bacteria is carried out by the gene nxrA, while the opposite reaction ($NO_3-$ to $NO_2-$) is carried out by narG. Yet the sequences from these genes are sufficiently similar to be grouped together in the KEGG database. Furthermore, narG is involved in two different metabolic pathways: dissimilatory nitrate reduction ($NO_3-$ to $NH_4$) and denitrification ($NO_3-$ to $N_2O$ or $N_2$). The analytics system 100 can use one or more different processes as described below to resolve the ambiguity of soil sequences.

In some embodiments, the analytics system 100 labels genes ambiguous, and several other genes may have similar ambiguity (e.g., pmo/amo genes, K10944, K10945, K10946, which may oxidize methane or ammonia). For example, as shown in Table 1 and Table 5 (below), there is a category for ambiguous nitrate reductases. The analytics system 100 processes genes such as these with ambiguous functions in one or more different ways (described below) with respect to derivation of gene counts and subsequent counts of metabolic pathways and soil health indicators.

In some embodiments, the analytics system 100 removes the counts of these ambiguous genes, which may be non-informative for metabolic pathway abundances. In other embodiments, the analytics system 100 examines, in soils, the correlation of these ambiguous genes with other non-ambiguous genes in a pathway, and assigns or splits the counts of the genes in a pathway accordingly.

In another embodiment, the analytics system 100 may process ambiguous gene categories by splitting the underlying sequences in the reference data to create new unambiguous categories. This may be accomplished, for example, through expert knowledge of the organisms performing these functions (and pruning of reference DNA sequences accordingly), or by construction of a phylogenetic tree of gene sequences, where coherent branches of related sequences are known to carry out given sub-functions.

C. Mixed Metabolic Signals Underlying Single Soil Functions

A different challenge with the formulation of soil health indicators occurs where a given function of soils relevant to agriculture is associated with multiple metabolic pathways, which are related by their net output but can present different signals in the environment. For purposes of explanation, the following example references data on functions representing nitrogen mineralization (i.e., conversion of organic nitrogen forms in soil organic matter to $NH_4$). The analytics system 100, in this example, uses nitrogen mineralization as an agronomic attribute (e.g., function) to determine an amount of nitrogen obtained by a crop from soil organic matter, which may reduce the need for additional fertilizer. The analytics system 100 uses a combination of agronomic, biogeochemical (e.g., nutrient cycling), and metabolic knowledge to curate relevant genes. For example, nitrogen mineralization may involve the breakdown of organic nitrogen containing compounds like proteins and amino acids.

In an embodiment, a list of the most directly relevant genes for proteases (protein degradation) includes those that are released extracellularly into soil by bacteria or neutral and alkaline proteases (npr and apr). These genes release urea from proteins, such that ureases (ure) may also be an indicator of protease activity. Moreover, the analytics system 100 considers urea transporter genes as an additional index of this activity. However, urea is also a form of nitrogen that may be commonly applied to soil in agriculture. An additional form of organic nitrogen in soils is chitin (degraded by the chi gene), a non-polymer protein found in insects and fungi. A common enzyme assay for nitrogen mineralization in biogeochemical studies of soil is NAG (N-aceyl-β-D-glucosaminidase), which measures potential degradation of chitin.

Each of the above described gene functions for microbial utilization of soil protein, urea, and chitin fall within the biogeochemical and agronomic descriptions of soil nitrogen mineralization. The analytics system 100 considers such consistency or prior (gene and metabolic) inconsistencies to determine a soil health indicator. The effectiveness of a soil health indicator in reflecting these processes may vary based on the mixture of one or more underlying processes, their individual responses to different soil chemical factors, or potential signal driven by other factors (e.g., shaping gene abundances) and environmental noise (e.g., unknown variation). Resolution of soil health indicator effectiveness and determination of the ideal gene and metabolic factors underlying an indicator of soil health may require data obtained from real world soil samples with characterized variation or data matching expected environmental controls (e.g., nitrogen mineralization rate data or chemical proxies like soil carbon-to-nitrogen ratios, and amino sugars). Further, the analytics system 100 determines the weights of underlying genes and metabolic pathways in an indicator by inspection of relationships or machine learning in data comparing soil genetic potential to expected environmental relationships.

D. Calculation of Soil Health Indicators

In various embodiments, the analytics system 100 determines soil health indicators by assigning soil DNA sequence data to the corresponding genes in reference databases, in order to determine counts of each gene within each soil sample. For example, the analytics system 100 may use bioinformatics processes to assign DNA sequences match to nitrogen mineralization genes (nprS, aprA, cynS, URE, ureA, ureB, ureC, urtA, urtB, urtC, urtD, urtE, HEX, HEXA B, csn, nagZ, sacC, cynS, chiA) as shown in Table 5 (below). The analytics system 100 may normalize gene counts by total reads or gene hits, rarifaction, normalization by single copy marker genes, or other transformations. The analytics system 100 may combine reads or normalized read counts within a protein where distinct subunits of a protein are represented. For example, in the urease gene, counts are represented as the mean counts for the three subunits (ureA, ureB, ureC). As another example, the nif gene for nitrogen fixation proteins is also composed of several subunits, nifH, nifD, nifK, nifW. The nifH subunit codes for the metalloprotein containing the active site of nitrogen fixation. The analytics system 100 uses these codes to index biogeochemical activity of nif. A different perspective on these genes is held from a biochemical perspective, where several organisms are known to harbor nifH genes, but are incapable of nitrogen fixation due to missing helper proteins from nifD, such that nifD might be considered a more suitable indicator of nitrogen fixation activity.

Once gene counts are determined, the analytics system 100 combines the counts into a function of the counts (e.g., an aggregate count) for a given metabolic pathway (e.g., nitrogen pathways in Table 1 and Table 5) of which these genes are members. For nitrogen mineralization, these pathways may include urea mineralization (URE, ureA, ureB, ureC), urea transporters (urtA, urtB, urtC, urtD, urtE), chitinases (HEX, HEXA B, csn, nagZ, sacC, cynS, chiA), and secreted proteases (nprS, aprA, cynS), as shown in Table 5. The analytics system 100 may weight, add, or eliminate from indicators these genes within each of the pathways based on relationships in agronomic data, for example, relative fit with rates of nitrogen mineralization.

The analytics system 100 represents or combines counts of metabolic pathways in one or more ways in an agronomic indicator of soil health, where nitrogen mineralization can be viewed as a source of nitrogen from soils (reducing the need for external fertilization of crops). Examples of different combinations of these pathways are shown in Table 1, which includes a list of pathways and corresponding metabolic class (e.g., nitrogen mineralization). Several other potential combinations of pathways are shown in Table 1, where soil health indicator levels (SHI levels 1, 2, and 3) represent increasing granularity, which may be more representative of the underlying biology. Useful indicators balance granularity to be representative of agronomic outcomes with clear interpretability.

In the example of nitrogen mineralization, at SHI level 1 (shown in Table 1), the analytics system 100 considers each pathway as a factor of soil nitrogen supply. SHI level 2 includes more granularity, which separates nitrogen mineralization into organic nitrogen (Proteases and Chitinases pathways) and urea mineralization (urea mineralization and transporters). SHI level 3 includes even further granularity, retaining separate metabolism for soil protein (Proteases), chitin (Chitinases), and urea (urea mineralization, here disregarding urea transporters). In each of these instances (SHI levels 1, 2, 3), the analytics system 100 aggregates gene hit counts within the metabolic pathways belonging to the indicator (SHI level category), after being aggregated from gene counts to pathway counts. This aggregation from pathways to indicators may be accomplished by calculation of a function (e.g., including ratios, averages, weighted sums, etc.), with weights obtained by elimination, manual curation, statistical fitting, or machine learning. The analytics system 100 uses the aggregated counts to determine soil health indicators (e.g., including crop or regional specific percentiles). The analytics system 100 may provide for display (on a client device) soil health indicators for a given farm or series of fields.

E. Example Soil Health Indicator for Nitrogen Mineralization

Figure 7:
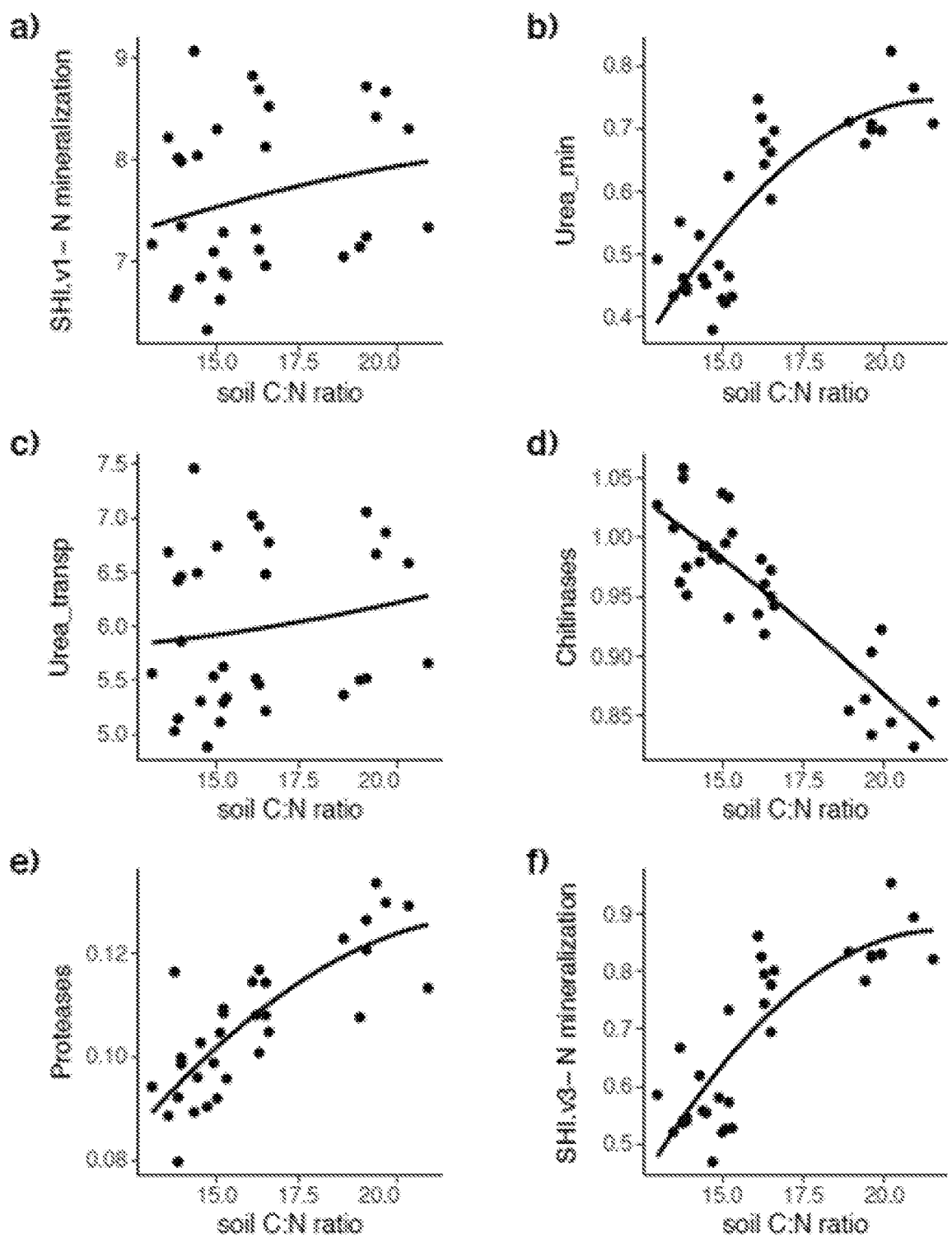
FIG. 7 illustrates soil health indicators for nitrogen mineralization according to an embodiment.

FIG. 7 illustrates soil health indicators for nitrogen mineralization according to an embodiment. In particular, FIG. 7 illustrates how the analytics system 100 may combine different metabolic pathways to determine a soil health indicator. FIG. 7 shows how different nitrogen metabolic pathways and indicator permutations relate to soil carbonto-nitrogen (C:N) ratio, which indicate increasing soil nitrogen limitation and may promote nitrogen mineralization.

Panel (a) shows that adding (e.g., normalized) gene count in pathways belonging to the nitrogen mineralization class does not provide a soil health indicator that tracks an expected increasing trend with soil C:N ratio. This ratio is thought to reflect soil and microbial nitrogen availability, and hence unmet demand for N driving energetically expensive nitrogen mineralization. Inspection of the underlying metabolic pathways reveals signals are mixed under this soil health indicator. For example, the class nitrogen mineralization includes (b) urea mineralization and (c) urea transporters. Panel (b) shows that the pathway for urea mineralization has an increasing relationship with soil C:N. On the other hand, panel (c) shows that urea transporters present no clear signal. As shown in panel (d), chitinase metabolism also has an inversely proportional relationship with soil C:N ratios. Panel (e) shows that secreted proteases have a proportional relationship with soil C:N ratios, as expected by first principles, with increasing C:N reflecting greater nitrogen scarcity.

The data in FIG. 7 show not only how a soil health indicator of agronomic function formed naively from metabolic information may not be reliable, but also how the analytics system 100 may use agronomic data and expert curation to determine an accurate soil health indicator. Panel (0 shows a soil health indicator resulting from the analytics system 100 refining the indicator formulation using real soil data. In this case, urea transporters are not only non-informative for the expected relationship, but also occur at high abundance in comparison to other genes, dominating the combined class level signal. Also, while chitinase metabolism has a strong relationship with soil C:N, mixing this metabolism with signals may weaken the resulting soil health indicator. Although chitin mineralization may be measured in soil biogeochemical enzyme assays, these assays were not developed in agronomic systems. Thus, chitin mineralization is not expected to be a dominant process of nitrogen mineralization in agricultural soils, despite the relatively greater abundance of these genes.

Having eliminated urea transporters and chitin as less relevant, the analytics system 100 determines the soil health indicator shown in panel (f) as the sum of urea mineralization (ureases) and secreted proteases. These metabolic pathways included in the resulting soil health indicator are internally consistent because urea results as the product of nitrogen mineralization in proteins. In addition, these metabolic pathways have consistent signals within agronomic soils, unlike other pathways of nitrogen mineralization (as shown in FIG. 7).

F. Nitrogen Cycling

Nitrogen cycling Soil Health Indicators calculated from functional gene data may represent various facets of the microbial nitrogen cycle in soil. These indicators may be broadly constructed to represent pathways of nitrogen loss, transformation, retention, or gain in agricultural soils. Nitrogen is a critical element for photosynthesis and plant biomass growth, and may be carefully managed in agricultural soils. Nitrogen cycling SHIs provide information on how added N fertilizer may be retained or lost through soil microbial processes, and may further indicate deficiencies or excess. This information can be used in agriculture to target fertilization rates to increase or maximize crop productivity while reducing or minimizing excess fertilizer use, which may increase costs and negatively impact water quality, for example.

Forms of nitrogen considered may include at least a part or the entire range of N oxidation states, including $N_2$, $N_2O$, $NO$, $NO_2^-$, $NO_3^-$, $NH_3^+$, $NH_4$, and organic (carbon-bound) N compounds (e.g. amino acids/proteins, chitin, nitrile, etc). Metabolic processes driving transformation among these forms broadly include denitrification, nitrification, uptake of nitrate and ammonium, utilization of urea, chitin, and proteins, and atmospheric nitrogen fixation.

Simplified representations of these cycles for communicating agricultural SHIs may include soil N loss, retention, and supply; mobilization, immobilization, nitrate retention, urea and organic N mineralization, and N-fixation, etc. Examples of simplified representations of agricultural Soil Health Indicators from major N cycling pathways are given in Table 1. A detailed list of genes and their identifiers linking to sequence databases are given for the major pathway categories in Table 5 in the Appendix. For nitrogen cycling genes, these tables further list genes with ambiguous functions which may be tracked by the analytics system 100.

Calculation of these example indicator values may be made by summing total normalized gene counts within each biological or hierarchical SHI grouping. For example, representation of broad biological classes may be derived from the sum of gene counts for each gene in each biological class in Table 5. However, this level of detail may be too fine for some agricultural applications, and more condensed SHIs shown in Table 1 can be calculated, for example, as the sum of counts of biological groupings within each coarser level SHI class shown in Table 1. In this embodiment, counts of genes are aggregated by biological classes using Table 5, then further aggregated into simplified SHIs using Table 1. In various embodiments, the SHI levels are organized by granularity. In the example shown in Table 5, Level 3 is providing more biological detail, and Level 1 is more agriculturally interpretable (e.g., to a farmer). In addition, Level 2 is intermediate complexity grouping between Level 1 and Level 3. Multiple levels are shown to illustrate the process of deriving which level or combination of biology and agronomy is potentially most suitable. The analytics system 100 can use data driven support to combine related biological cycles without canceling or reducing signals carried by the underlying biology.

However, data transformations underlying SHI calculations are not limited to the hierarchies in these tables, and may further include calculation of ratios, averages, weighted sums, etc., including statistical fitting or machine learning. For example, indication of a process rate for denitrification may involve several factors represented by individual SHIs. This process may depend on genes SHIs for one or more of denitrification, nitrification, carbon availability, and oxygen availability. Machine learning (i.e., LASSO regression) may be used to fit the best combination of weights for genes or SHIs using a validation dataset.

TABLE 1

Table 1: Example categories used in soil health indicators for agricultural nitrogen cycling, as derived from gene counts belonging to each pathway obtained from soil DNA sequencing. Indicators can be formulated as normalized counts of these indicators, ratios, weighted sums, etc. Here, several abbreviations are given for nitrogen cycling pathways and SHIs to conserve space, and these exactly match detailed gene tables in the appendices. For example, an additional Class of nitrogen cycling genes "Ambig_NO3r" here indicates a group of nitrate reductases with ambiguous membership in multiple pathways (shown beneath the horizontal line). Abbreviations under Pathway include: denitrification (N DNT) ammonia oxidation (NH3_oxid, also part of nitrification), nitrate transporters (NO3_transp) and assimilatory reduction (NO3_A_red), ammonium assimilation (NH4_assim), dissimilatory nitrate reduction (NO3_D_red, also known as DNRA), urea mineralization (Urea_min) and transporters (Urea_min), and nitrogen fixation (N2_fix). Other abbreviations are used in this table to conserve space including mineralization (min), and immobilization (immob).

| Class | Pathway | SHI level 1 | SHI level 2 | SHI level 3 |
|---|---|---|---|---|
| Denitrification | N_DNT | soil N loss | Mobilization & loss | Denitrification |
| Nitrification | NH3_oxid | soil N loss | Mobilization & loss | Nitrification |
| Immobilization | NO3_transp | soil N retention | Immobilization | NO3 Immob. |
| Immobilization | NO3_A_red | soil N retention | Immobilization | NO3 Immob. |
| Immobilization | NH4_asim | soil N retention | Immobilization | NH4 Immob. |
| Ammonification | NO3_D_red | soil N retention | nitrate retention | Ammonification |
| Mineralization | Urea_min | soil N supply | urea_mineralization | urea_min. |
| Mineralization | Urea_transp | soil N supply | urea_mineralization | — |
| Mineralization | Chitinases | soil N supply | Organic N min. | — |
| Mineralization | Proteases | soil N supply | Organic N min. | Soil protein |
| N_fixation | N2_fix | soil N supply | N fixation | N fixation |
| Ambig_NO3r | — | — | — | — |

G. Phosphorus Cycling

Phosphorus cycling Soil Health Indicators calculated from functional gene data may represent various processes of microbial phosphorus cycling in soil. These indicators may be broadly constructed to represent pathways of phosphorus transformations including microbial uptake, mineral P solubilization, or mineralization of various organic P forms in agricultural soils. Phosphorus is a critical element for plant biomass growth, and may be carefully managed in agricultural soils. Phosphorus cycling SHIs may indicate soil P deficiencies or P available to be mineralized by microbes for plant use. This information can be used agriculture to target fertilization rates to increase or maximize crop productivity while reducing or minimizing excess fertilizer use, which may increase costs and negatively impact water quality.

Forms of phosphorus considered may include free inorganic orthophosphate ($PO_4^{2-}$) or $PO_4^{2-}$ bound to minerals containing cations e.g., $K^+$, $Ca^{2+}$, $Mn^{2+}$, $zn^{2+}$, $Fe^{3+}$, $Al^{3+}$. Potential utilization of organic P forms like phytate, phosphonates, etc. may also be represented in gene based soil health indicators, as are various forms of high and low affinity phosphorus transporters (active and passive transport, respectively).

Simplified representations of these metabolic process for agricultural management may include as examples: counts or ratios of P uptake vs. P scavenging; P transporters vs. mineral P solubilization vs. organic P hydrolysis, etc. (Table 2). Each of these broad biologically based categories represents a collection of metabolic pathways, genes, and enzymes shown in detail in Table 6.

Calculation of these example indicator values may be made by summing total normalized gene counts within each biological or hierarchical SHI grouping. For example, broad biological classes may be derived from the sum of gene counts for each gene in each biological class in Table 6, which may be further aggregated into simplified SHIs using mapping shown in Table 2. However, data transformations underlying SHI calculations are not limited to the simple hierarchies in these tables and may further include calculation of ratios or weighted sums, averages, or ratios, including statistical data fitting by regression or machine learning.

TABLE 2

Table 2: Example categories used in soil health indicators for agricultural phosphorus cycling, as derived from gene counts belonging to each pathway obtained from soil DNA sequencing. Indicators can be formulated as normalized counts of these indicators, ratios, weighted sums, etc. Several abbreviations are used in this table to maintain consistency of labeling with the detailed list of P cycling genes provided in the Appendix Table 6, particularly for Class and Pathway levels of the hierarchy which correspond directly to that table. Class level abbreviations for P cycling include immobilization (P immobil), solubilization (solubil) and scavenging (P scav) processes. Pathway abbreviations include inorganic P transporters (P transp), inorganic phosphatases (Inorg_Pase), P solubilization (P solubil), Glycerol-3-phosphate (glyc_3_pase), phosphatases (P_ases), and phosphonate transporters (phn_transp.) and degradation (phn_degrad.).

| Class | Pathway | SHI level 1 | SHI level 2 |
|---|---|---|---|
| P_immobil | P_transp | P_immobil | P immobil |
| P_solubil | Inorg_Pase | Polyphosphate | Polyphosphate |
| P_solubil | Inorg_Pase | P_scavenging | Inorganic Pase |
| P_solubil | P_solubil | P_scavenging | P solubilization |
| P_scav | Glyc_3_pase | P_scavenging | — |
| P_scav | P_ases | P_scavenging | Phosphatases |
| P_scav | phn_transp. | P_scavenging | — |
| P_scav | phn_degrad | P_scavenging | Phosphonates |

H. Carbon Cycling

Carbon cycling Soil Health Indicators calculated from functional gene data may represent microbial potential to utilize various carbon substrates, for example, that are the primary constituents of soil organic matter. These SHIs are biological indicators of the relative availability of carbon for microbial decomposition, or inversely soil carbon resistance to breakdown and potential for its retention as soil organic matter. Carbon availability or retention may be of considerable interest for management of agriculture soils, as available C may drive microbial mediated processes e.g., nitrogen mineralization or microbial immobilization. Retention of soil carbon by the accumulation of less available forms (e.g., often utilized by microbes with slower metabolism) is which may be further aggregated into simplified SHIs using mapping shown in Table 3. However, data transformations underlying SHI calculations are not limited to the simple hierarchies in these tables, and may further include calculation of ratios or weighted sums, averages, or ratios, including statistical data fitting by regression or machine learning.

TABLE 3

Table 3: Example categories used in soil health indicators for agricultural carbon availability, as derived from gene counts belonging to each pathway obtained from soil DNA sequencing. Indicators can be formulated as normalized counts of these indicators, ratios, weighted sums, etc. Several carbon Compound classes for which microbial degradation genes are known have been abbreviated here. The Class Sugars (Compound: C_sug_) includes: sucrose/glucose (sucr); lactose (lact), galactose (gal), trehalose (treh), rhamnose (rham), and arabinose (arab). The Class polymers (C_poly_) includes cellulose (cellul.) hemicellulose (hemi), xylose (xylos), chitin, pectin, and lignin. Aromatic compounds (C_arom_) are a convenience category which includes some carboxylases, but also genes for degradation of several other aromatic classes including "other", nitroaromatics (nitro), "BTEX" type compounds (e.g., benzene, toluene, ethylbenzene and xylene), and polyaromatic hydrocarbons (PAH).

| Class | Compound | SHI level 1 | SHI level 2 | SHI level 3 | Level 3 weight |
|---|---|---|---|---|---|
| Sugars | C_sug_sucr | Available C | Carbohydrate | simple_sugar | 1 |
| Sugars | C_sug_lact | Available C | Carbohydrate | simple_sugar | 1 |
| Sugars | C_sug_gal | Available C | Carbohydrate | simple_sugar | 1 |
| Sugars | C_sug_treh | Available C | Carbohydrate | complex_sugar | 2 |
| Sugars | C_sug_rham | Available C | Carbohydrate | complex_sugar | 2 |
| Sugars | C_sug_arab | Available C | Carbohydrate | complex_sugar | 2 |
| Polymers | C_poly_starch | Available C | Carbohydrate | starch | 3 |
| Polymers | C_poly_cellul | Available C | C Polymer | cellulose | 4 |
| Polymers | C_poly_hemi | Resistant C | C Polymer | resistant_biomass | 5 |
| Polymers | C_poly_xylos | Resistant C | C Polymer | resistant_biomass | 5 |
| Polymers | C_poly_chitin | Resistant C | C Polymer | resistant_biomass | 5 |
| Polymers | C_poly_pectin | Resistant C | C Polymer | resistant_biomass | 5 |
| Polymers | C_poly_lignin | Resistant C | Recalcitrant C | lignin | 7 |
| Aromatic | C_arom_carbox | Resistant C | Recalcitrant C | carboxylics | 8 |
| Aromatic | C_arom_other | Resistant C | Recalcitrant C | aromatics | 9 |
| Aromatic | C_arom_nitro | Resistant C | Recalcitrant C | aromatics | 9 |
| Aromatic | C_arom_BTEX | Resistant C | Recalcitrant C | aromatics | 9 |
| Aromatic | C_arom_PAH | Resistant C | Recalcitrant C | poly_aromatics | 10 | of also of considerable agricultural interest as soil carbon accumulation can promote soil water retention along with microbial biomass that can help retain added nutrients and support plant beneficial microbes.

Carbon cycling SHIs represent pathways responsible for the breakdown of major soil carbon classes, including simple and complex polymer carbohydrates and polysaccharides, cellulose, hemicellulose, lignin, and various alkane and aromatic compounds. For the purposes of informing agricultural management practices, simplified indices like carbohydrate to aromatic gene ratios, or normalized counts of these groups or finer scale categories may be of interest.

Example formulations of simplified categories for communication of agricultural soil health indicators are shown in (Table 3). Each of the soil carbon compound classes represented therein may be degraded by enzymes which are encoded by numerous microbial genes (Table 7). These finer scale categories may also be of interest for informing predictions of other element cycles like nitrogen or phosphorus, given the potential overlap of groups of microbes specializing in certain transformations of both carbon and nutrients.

Calculation of these example indicator values may be made by summing total normalized gene counts within each biological or hierarchical SHI grouping. For example, broad biological classes may be derived from the sum of gene counts for each gene in each biological class in Table 7, I. Oxygen Availability Soil oxygen availability may be of agricultural interest given the role of higher or lower oxygen availability in cycling of nitrogen, phosphorus, or carbon, or waterlogging and anaerobic effects on plant root growth and rot. Microbial indicators of oxygen availability, for example, might reveal soils are poorly drained, with potential agricultural interventions including altered tillage, addition of mineral or organic materials to improve soil structure and drainage, or engineering solutions like drainage ditches, tile drainage, or altered to irrigation rates or timing.

Oxygen availability Soil Health Indicators calculated from functional gene data may represent the prevalence of oxygen in soil, as reflected by the presence of genetic elements involved in various microbial respiration pathways. These pathways may include aerobic respiration (including low and high affinity systems) and pathways of anaerobic metabolism including denitrification, iron reduction, sulfate reduction, and methanogenesis from organic substrates or $H_2/CO_2$ reduction.

Simplified representations of oxygen availability from the relative abundance of these pathways may include aerobic and anaerobic gene counts or ratios, further consideration of microaerobic or individual pathways, or even weighted sums of pathways, given the ability to multiply gene counts by quantitative scales based on the redox potential or free energy yield of these pathways, or scaled representations thereof (Table 4). Individual genes comprising each respiratory pathway in this SHI are shown in Table 8, compiled by translating genes into KEGG or Pfam identifiers used to retrieve counts from gene annotation tools.

Calculation of these example indicator values may be made by summing total normalized gene counts within each biological or hierarchical SHI grouping. However, data transformations underlying SHI calculations are not limited to the simple hierarchies in these tables, and may further include calculation of ratios or weighted sums, averages, or ratios, including data fitting machine learning.

The analytics system 100 receives 210 metadata describing a soil sample 275. In some embodiments, the metadata may indicate one or more crops grown in a geographical location having the soil sample 275. Example types of crop include corn, soybean, lettuce, strawberry, potato, among other types of fruits, nuts, vegetables, or plants. The cropping history of a geographical location may include a rotation of multiple types of crops, e.g., based on seasonality or the geographical location. In other embodiments, the metadata may indicate other information such as the geo-

TABLE 4

Table 4: Example categories used in soil health indicators for agricultural oxygen availability, as derived from gene counts belonging to each pathway obtained from soil DNA sequencing. Indicators can be formulated as normalized counts of these indicators, ratios, weighted sums, etc. Here, an example weighting scheme is shown, corresponding to levels in the biological pathways. Additional indicators can be derived by using the sum of weighted counts across each pathway. Abbreviations for Electron acceptors tabulated include nitrate reductases (o_NO3_red), ferric iron reductases (Fe_reduct), genes which belong to multiple anaerobic pathways or are not distinguishable among them (Ambig anaerob), dissimilatory sulfate reduction (S_dissim). Abbreviations for oxygen availability Pathways include genes for respiring at high, ambiguous, or low oxygen tension (O2_high, O2_ambig, and O2_low, respectively; for various reductive respiratory pathways utilizing nitrate including Denitrification, nitrate reduction (Nitrate reduct), and dissimilatory nitrate reductases (Diss_NO3_red); for ferric iron reduction (Fe_reduct) or genes with ambiguous assignments to anaerobic pathways for iron, nitrate or sulfur (Ambig_Fe_NO3_S); for dissimilatory sulfate reduction (Diss_SO4_red). Several methanogenic Pathways are described based on the substrate used as the electron acceptor, including acetate (Acetoclastic), methanol, methylamine, genes that are not pathway specific but present in all archaeal methanogens (Archaeal CH4), or those specific to the use of a $CO_2/H_2$ pair for respiration (Hydrogenotrophic).

| Electron acceptor | Pathway | SHI level 1 | SHI level 2 | SHI level 3 | Weight |
|---|---|---|---|---|---|
| Aerobic | O2_high | aerobic | aerobic | well drained | 100 |
| Aerobic | O2_ambig | aerobic | aerobic | NA | 93.75 |
| Aerobic | O2_low | aerobic | aerobic | moderate drainage | 87.5 |
| o_NO3_red | Denitrification | anaerobic | anaerobic | somewhat poorly drained | 81.25 |
| o_NO3_red | Nitrate reduct | anaerobic | anaerobic | somewhat poorly drained | 81.25 |
| o_NO3_red | Diss_N03_red | anaerobic | anaerobic | somewhat poorly drained | 81.25 |
| Fe_reduct | Fe_reduct | anaerobic | anaerobic | somewhat poorly drained | 50 |
| Ambig anaerob | Ambig_Fe_NO3_S | anaerobic | anaerobic | NA | 50 |
| S_dissim | Diss_SO4_red | anaerobic | very anaerobic | very poorly drained | 25 |
| Methanogen | Acetoclastic | anaerobic | very anaerobic | very poorly drained | 0 |
| Methanogen | Methanol | anaerobic | very anaerobic | very poorly drained | 0 |
| Methanogen | Methylamine | anaerobic | very anaerobic | very poorly drained | 0 |
| Methanogen | Archaeal CH4 | anaerobic | very anaerobic | very poorly drained | 0 |
| Methanogen | Hydrogenotrophic | anaerobic | very anaerobic | very poorly drained | 0 |

III. Example Process Flows

Figure 2A:
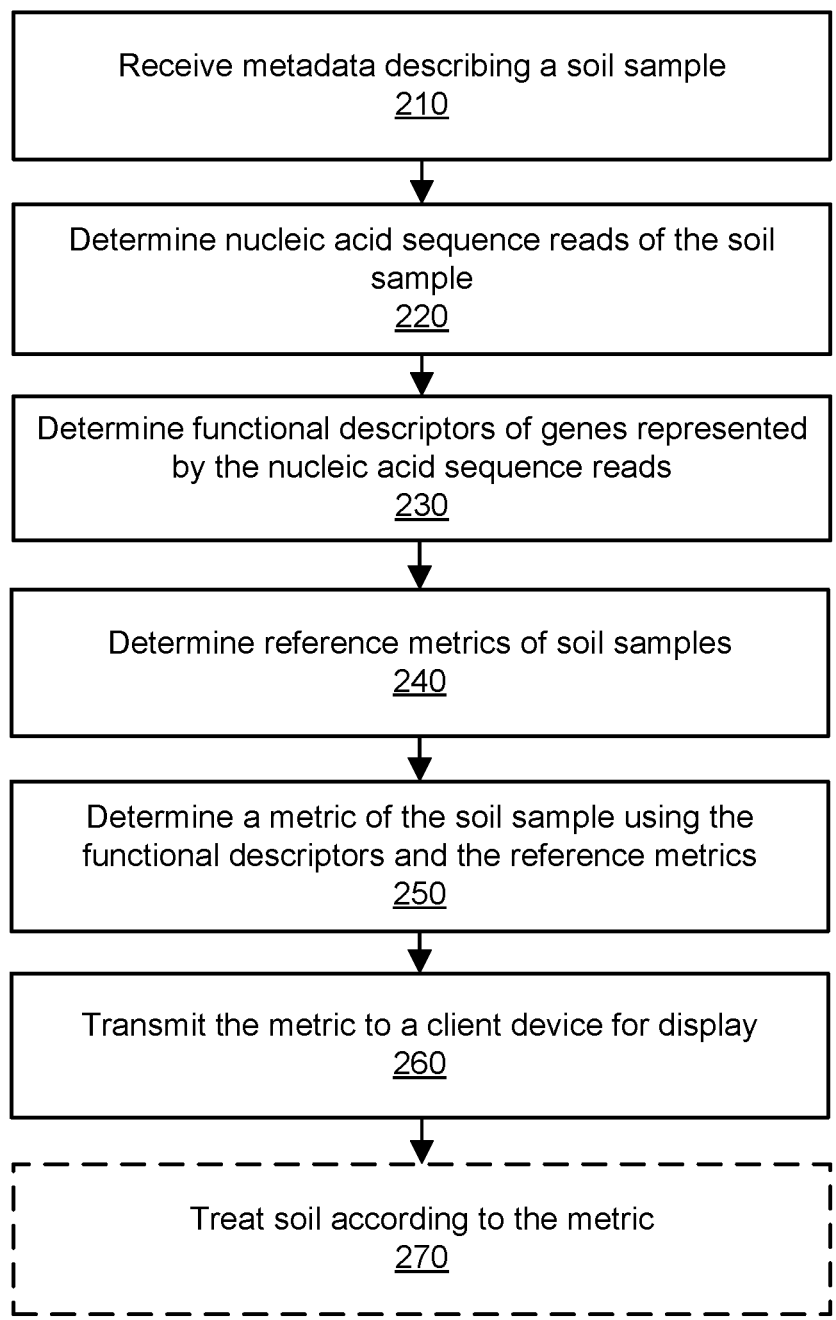
FIG. 2A illustrates an example process for providing a metric of a soil sample according to an embodiment.
Figure 2B:
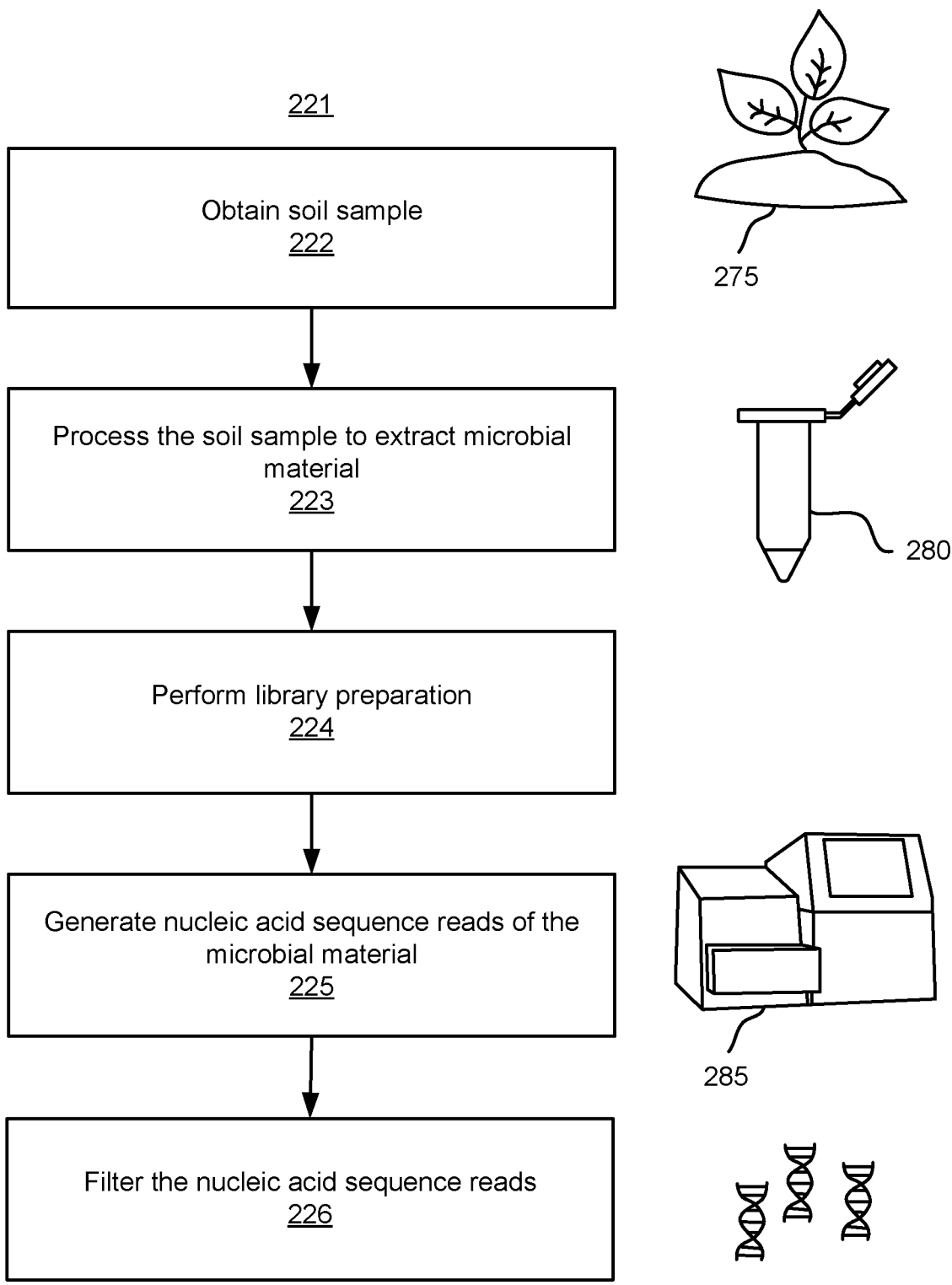
FIG. 2B illustrates an example process for determining nucleic acid sequence reads of a soil sample according to an embodiment.

FIG. 2A illustrates an example process 200 for providing a metric of a soil sample according to an embodiment. FIG. 2B illustrates an example process 221 for determining nucleic acid sequence reads of a soil sample 275 according to an embodiment. In various embodiments, the processes 200 or 221 are used by the analytics system 100 within the system environment in FIG. 1. The processes may include different or additional steps than those described in conjunction with FIG. 2A-B in some embodiments or perform steps in different orders than the order described in conjunction with FIG. 2A-B.

graphical location, a current crop grown in the geographical location, or attributes describing treatment of the soil sample 275. The geographical location may be defined by global positioning system (GPS) coordinates or other suitable information, e.g., a neighborhood, city, state, country, or identification number. Example attributes describing treatment of the soil sample include agricultural techniques such as no-till farming, use of a cover crop to manage soil qualities (e.g., erosion, fertility, disease, or biodiversity), carbon farming, strip-till, and conservation agriculture. Attributes may also describe water or fertilizer usage, whether a crop is organic, temperature, precipitation, or climate, among other types of crop or soil related information. Metadata may also indicate a soil type of the soil sample 275. The analytics system 100 may process soil samples of different soil types, for example, sandy, silt, clay, loamy, and peat, among others. Additionally, the analytics system 100 may store soil chemical data including soil pH, carbon, and nutrients (e.g., nitrogen or nitrate, ammonium, phosphorus or phosphate, potassium, and calcium concentrations, among others).

The analytics system 100 determines 220 nucleic acid sequence reads of the soil sample 275. Referring now to FIG. 2B, the process 221 may be performed to determine the nucleic acid sequence reads as part of the process 200 of FIG. 2A.

A soil sample 275 is obtained 222 using any of the methods previously described with reference to FIG. 1, e.g., the analytics system 100 receives the soil sample 275 from a farmer using a sampling tube 280. The soil sample 275 is processed 223 to extract microbial material (also referred to as microbial genetic material). In some embodiments, the soil sample 275 may be stored at −80 degrees Celsius prior to extraction of the microbial material. In an embodiment, the soil samples are added to extraction vessels by mass, volume, suspension volume, or another measurement. Cell lysis is performed on the soil samples to release the microbial material including intracellular nucleic acids. Cell lysis may include chemical (buffers or salts), mechanical (bead beating or sonication), or thermal (e.g., freezing, free-thaw cycling, or microwaving) processes. Soil and the released microbial material are separated. Cellular debris may be removed using chemical precipitation or centrifugation. Additionally, contaminants may be removed using precipitation and elution of the microbial material. The microbial material may be prepared using fluorescent dyes or gels for downstream assay or spectroscopy.

In some embodiments, the nucleic acids of the microbial material may be processed prior to library preparation. For example, target genes or genome regions may be enriched for polymerase chain reaction (PCR) amplification or amplicon sequencing. Targeted DNA primers may be used to flank a region of interest. Alternatively, in shotgun sequencing, the microbial material may be prepared for sequencing of the entire content, e.g., microbes in a crop community of the processed soil sample. In some use cases, DNA fragment size may be controlled chemically using size selection gel beads, physically using ultrasonic shearing, or enzymatically using transposase fragmentation.

Sequencing library preparation is performed 224 on the extracted microbial material. Library preparation may include attaching sequencing adapters or tags to nucleic acids to facilitate reading of the nucleic acids. Sequencing tags may be unique to each sample (e.g., serving as a barcode) and enable identification of sequenced data associated with each sample in a multiplexed run with multiple samples. Libraries may also be prepared using other suitable methods such as ligation or transposase. In some use cases, library preparation includes protocols from sequencer original equipment manufacturers (OEMs), third party kit providers, or other resources. The analytics system 100 may store data from library preparation for future processing or analyses of other soil samples.

Once the sequencing library is prepared, the library or a portion of the library can be sequenced such that nucleic acid sequence reads of the microbial material are generated 225 using one or more techniques. In some embodiments, a sequencer 285 performs sequencing (e.g., of DNA or RNA) and outputs sequence reads of the microbial material. The sequencer 285 may provide the output sequence reads to the analytics system 100. The sequencer 285 can be communicatively coupled to the analytics system 100 through a wireless, wired, or a combination of wireless and wired communication technologies. In some embodiments, the nucleic acid sequence reads are generated using next generation sequencing (NGS) techniques including synthesis technology (ILLUMINA®), pyrosequencing (454 LIFE SCIENCES), ion semiconductor technology (Ion Torrent sequencing), single-molecule real-time sequencing (PACIFIC BIOSCIENCES®), or nanopore sequencing (OXFORD NANOPORE TECHNOLOGIES). DNA sequencing can also be performed as described in Sanger et al. (PNAS 74:5463, (1977)) and the Amersham International plc sequencing handbook, which methods are incorporated by reference herein. The analytics system 100 filters 226 the nucleic acid sequence reads, e.g., for quality control. In particular, the analytics system 100 may remove sequence reads having artificial multiplexing barcode or adapter sequences. In addition, the analytics system 100 may determine that a sequence read is low quality responsive to determining that a length of the sequence read is less than a threshold value, the sequence read includes at least a threshold number of ambiguous bases, or a read quality score (e.g., determined using a third-party tool) is less than a threshold score. The analytics system 100 may discard low quality sequence reads. The analytics system may also partition sequence reads using identification barcodes for demultiplexing batches of sequence reads generated from multiple samples.

Returning to FIG. 2A, the analytics system 100 may use the sequence reads to identify presence of one or more types of functional genes in the soil sample. For example, the analytics system 100 can align the sequence read to one or more reference genomes that are stored in the reference database 104 (e.g., reference genomes of functional genes commonly found in soil or otherwise known). The reference genome provides the context as to the position in a genome from which the nucleic acid fragment originates. The analytics system 100 can align the sequence reads to known sites in the sequences of different organisms, which may be typically found in soil samples. Based on this, the analytics system 100 can identify which functional genes are present in the soil sample, and can also gain information about functional genes that are not present.

The analytics system 100 then determines 230 functional descriptors of the genes represented by the nucleic acid sequence reads. In various embodiments, a functional descriptor may be a functional gene measure in a soil sample. A functional descriptor may also be a metabolic pathway or SHI, or a collection of genes thereof. The analytics system 100 may store the functional descriptors in the gene database 106, e.g., in a table or another suitable type of data structure. In one embodiment, for each nucleic acid sequence read of at least a subset of the nucleic acid sequence reads, the analytics system 100 determines functional descriptors of the microbial gene associated with the nucleic acid sequence read.

In an embodiment, the analytics system 100 determines microbial functional genes present in the soil sample 275. For each of the present functional genes, the analytics system 100 determines a measure (e.g., count) of the functional gene in the soil sample 275. The analytics system 100 may normalize the measure using a total measure of functional genes in the soil sample, e.g., by dividing individual counts over a total count. In other embodiments, the analytics system 100 may normalize based on total sequence reads per sample, total annotations, total genome copies measured, etc. Normalization of the counts may account for sources of systematic variation or error in the counts, e.g., as stored in a table or another type of data structure. In other embodiments, instead of using nucleic acid sequencing, the analytics system 100 determines counts of organisms' functions using quantitative PCR (qPCR) or Droplet Digital PCR (ddPCR).

In some embodiments, data on the genetic functional potential of soil microbes is determined by comparing quality control filtered sequence reads from soil DNA to a reference database, e.g., using bioinformatics tools.

In some embodiments, the reference database contains genomic DNA sequence reads from known microorganisms, and information on functions (identity) of genes corresponding to these sequences. Examples of these databases may include NCBI's RefSeq database, the UniProt, Interpro, Pfam, SEED, COG, or KEGGs databases, etc. Databases may contain different systems of organizing genes (gene ontologies) into unique functional units (gene or protein identifiers). Genomic databases may also contain DNA sequence read data from multiple organisms for each gene or protein. Some databases may represent genes as consensus sequences or models (e.g., Pfam).

In some embodiments, identification of soil sample DNA sequence read queries by comparison to a reference database is made by a bioinformatics "pipeline." These software pipelines are characterized by the ability execute multiple DNA read processing tasks in sequence, e.g., quality filtering and demultiplexing of raw sequencer data, determination of functional attributes, normalization and tabulation, etc. Such pipelines may contain public or proprietary software tools, with or without custom modifications including packaging to orchestrate handoffs between programs. Tools for identifying reads by matching the reference database (gene annotation) may use various methods including exact or fuzzy matching of DNA or more often translated protein sequences, or "k-mers" unique strings of sequences.

Examples of read annotation tools include BLAST, LAST, RapSearch2, DIAMOND, etc. Alternately, gene annotations may be determined using consensus probabilistic models (e.g., hidden Markov models) instead of alignment to genes of different taxa, e.g., using HMMer. Results from of these methods may be returned as a table representing the best matching gene annotation for each sequence read, along with a quality score. These read tables may be filtered to retain high confidence scoring gene hits, using metrics like bit score, e-value, match percent identity, etc.

In some embodiments, read tables are subsequently processed to obtain a table of counts for each gene present for each sample considered, and may be normalized. Gene count tables are compiled by aggregating read tables by their corresponding gene annotations. These gene count tables may be normalized by a variety of methods including total gene counts, sequence read depth or single copy maker genes in each sample, or other methods including centered log ratios.

In some embodiments, normalized gene count tables are used to obtain various Soil Health Indicators (SHIs). Genes counts used in the calculations for these SHIs are obtained for each sample from gene count tables, then raw SHIs values are calculated for each sample.

In some embodiments, raw SHI values are further scaled to their community percentile values, based on their crop communities. For example, each sample is assigned a crop community based on cropping, management, and geospatial (GPS) location. For each crop community, a database is compiled of raw SHI values for samples previously analyzed with correspondingly similar crop and location reported at the time of their collection. Each new sample may be given a community percentile value for each SHI or SHI category, based on the rank percentile of a given raw sample SHI among corresponding SHIs in the community database. Other data transformations may be applied prior to or following calculation of community percentile values.

The analytics system 100 determines 240 reference metrics of soil samples, e.g., from geographical locations or communities in which the one or more types of crop were grown. The reference metrics may include a distribution of values of soil health indicators retrieved from the soil health indicators database 102. Generally, the analytics system 100 may retrieve the reference metrics (or "crop community values") from soil health indicators determined for soil samples of other users of the analytics system 100 or from other sources of reference information. For example, the analytics system 100 determines reference metrics from other soil samples within a threshold distance (e.g., 10, 50, 100, or 200 miles) from the soil sample. In a different example where the metadata indicates cropping history, the analytics system 100 determines reference metrics from other soil samples in which at least one common crop is currently or was previously grown. The analytics system 100 may use crop rotation systems as a basis for these community metrics, for example, corn-soybean rotations compared to continuous corn cultivation over consecutive years in a given geographical area. Furthermore, the analytics system 100 may determines reference metrics from other soil samples treated with similar or same agricultural techniques as those treated to the soil sample.

The analytics system 100 determines 250 a metric of the soil sample 275 using the functional descriptors and the reference metrics. The metric may be a measure of an agronomic attribute of the soil sample 275 or the soil at the geographical location generally. In an embodiment, the analytics system 100 determines a value of a soil health indicator using the functional descriptors. As previously described, the soil health indicator may be calculated as the function of measures of one or more types of microbial metabolic genes, e.g., associated with nitrogen or phosphorous cycling, utilization of different forms of carbon, or indicators of oxygen availability, plant growth promoting bacteria, root disease resistance, or post-harvest disease susceptibility. The analytics system 100 may determine the metric by performing one or more statistical transformations of the value of the soil health indicator. For example, the analytics system 100 determines a percentile of the value of the soil health indicator with respect to a distribution of soil health indicator values, as provided by the reference metrics. The percentiles may be scaled from 0 to 100%. In other embodiments, the analytics system 100 scales the value of soil health indicator to a different range such as 0.0 to 1.0 or 0 to 10, which may not necessarily be a percentile range.

In some embodiments, the analytics system 100 determines ranges of the reference metrics. The analytics system 100 may organize values of a soil health indicator for a set of fields (e.g., based on reference information of a community), within a threshold geographical location (or having another common characteristic or metadata), into buckets of a range of percentiles. For example, one bucket includes the top 10% of values of a soil health indicator associated with capacity of a given nutrient. Another bucket includes the next 10% of values of the soil health indicator, and so forth until a bucket including the bottom 10% of values of the soil health indicator. In other embodiments, the buckets may be associated with different intervals such as 20%, 25%, or 50%. When determining the metric for the soil sample, the analytics system 100 may identify a bucket to which the value of the soil health indicator of the soil sample belongs. For instance, the analytics system 100 determines that the value, of the soil health indicator of the soil sample collected from a geographical location, falls within the top 10% of values for nitrogen capacity of farms in the geographical location. Accordingly, the analytics system 100 may determine "0-10%" or "10%" as the metric.

In a different embodiment, the analytics system 100 may determine the metric according to standard deviations of the value of the soil health indicator away from an average value of the soil health indicator based on reference metrics. In some embodiments, the analytics system 100 may normalize the reference metrics to a logarithmic scale.

The analytics system 100 transmits 260 the metric to a client device 110 for display on a user interface, e.g., as shown in FIG. 7. In some embodiments, the analytics system 100 provides the metric for display in context of reference metrics. For example, a bar graph indicates an average value of a soil health indicator for farms in a geographical location from which the soil sample was collected. The user interface shows whether the metric is above, at, or below the average value. In other embodiments, the user interface may show other thresholds in varying levels of granularity, e.g., top 10% of values or top quartile or values of the soil health indicator based on reference metrics. In some embodiments, the analytics system 100 may provide a notification to a user responsive to determining that the metric is below a threshold value such as the average value. The notification may inform the user that treatment should be applied to a field, e.g., to supplement a nutrient at low availability. Alternatively, the analytics system 100 may use the metric and threshold to determine a specific agronomic recommendation. For example, where denitrification or nitrification (promoting loss of nitrogen fertilizer) are sufficiently high, it may be economically more efficient to add fertilizer in the spring rather than fall, or apply a denitrification inhibitor. By providing soil health indicators with community context, users of the analytics system 100 may determine health or performance of their fields relative to other comparable fields in terms of geographical location, cropping history, soil treatments, among other traits encoded in metadata stored by the analytics system 100. Additionally, the analytics system 100 may store determined metrics or soil health indicators in the soil health indicator database 102. The analytics system 100 may use these metrics or soil health indicators as reference metrics for subsequent determination of new metrics for other soil samples.

In an optional step in some embodiments, soil at the geographical location (from which the soil sample 275 is obtained) is treated 270 according to the metric. For example, the metric may indicate that a crop has lower levels of nutrients in comparison to average levels for crops of the same or similar type, or crops grown in similar conditions or geographical locations. In response, a farmer may provide additional fertilizer, fumigation, water, cover crop, or other types of substances to the crop or soil to modify levels of oxygen, nitrogen, phosphorous, potassium, or carbon of the soil. In some embodiments, the analytics system 100 may receive new soil samples from a field after a treatment is applied to the field, e.g., according to metrics or recommendations provided by the analytics system 100. The analytics system 100 determines updated metrics (or recommendations) by processing the new soil samples and transmits the updated metrics to the client device 110 for presentation. Thus, the farmer may evaluate effect of the treatment by comparing the metrics before and after applying the treatment. The analytics system 100 may also receive additional soil samples from a field continuously over a period of time (e.g., weekly, monthly, or at arbitrary sample collection times) and track performance or health of the field by identifying trends in the determined metrics. The analytics system 100 may determine trends in context of crop community data.

In one embodiment, the analytics system 100 may provide a command to a client device 110 or another type of device to automatically treat the soil with a treatment loaded onto the device. For instance, the device is a manned or autonomous tractor for applying fertilizer, water, or other substance to soil or crops.

FIG. 8 illustrates an example process 800 for determining a measure of an agronomic attribute according to an embodiment. The process 800 may include different or additional steps than those described in conjunction with FIG. 8 in some embodiments or perform steps in different orders than the order described in conjunction with FIG. 8.

In an embodiment, the analytics system 100 determines 810 nucleic acid sequence reads of genetic material in a soil sample (e.g., soil sample 275 as shown in FIG. 2B) from a geographical location (e.g., using a sampling tube 280 as shown in FIG. 2B). The genetic material may originate at least from one or more microbes from the soil sample. The soil at the geographical location may be part of an agricultural field where one or more crops are grown, or part of a fallow field where no crops have been grown (at least for a certain period of time).

The analytics system 100 determines 820, by processing the nucleic acid sequence reads (e.g., using a sequencer 285 as shown in FIG. 2B), a first set of measures of gene functions represented in the nucleic acid sequence reads. The analytics system 100 determines 830, by processing the gene functions, a second set of measures of metabolic pathways of microorganisms present in soil at the geographical location. Determining the second set of measures of metabolic pathways may include determining sums, weighted sums, or non-linear functions of measures of constituent genes from the gene functions. The analytics system 100 determines 840, by processing the measures of metabolic pathways, a third set of measures of soil health indicators of the soil at the geographical location. Determining the third set of measures of soil health indicators may include determining one or more functions (e.g., linear or non-linear) of the metabolic pathways corresponding to the nucleic acid sequence reads. The soil health indicators may include multiple levels of granularity. For example, the levels include a level closer to biological attributes and another level closer to agronomic attributes. The levels may also include an intermediate level representing a level between biological attributes and agronomic attributes.

The analytics system 100 determines 850 a measure of an agronomic attribute of the soil at the geographical location as a function of the first, second, and third sets of measures. The agronomic attribute describes an aspect of the soil related to crop production. In one example, the agronomic attribute is nitrogen mineralization and the plurality of metabolic pathways includes at least secreted proteases and urea mineralization.

In other embodiments, the analytics system 100 does not necessarily use all three sets of the measures. For example, the analytics system 100 may determine the measure of the agronomic attribute using measures of gene functions and soil health indicators, without having to use measures of metabolic pathways. In some embodiments, the analytics system 100 may also filter out at least one metabolic pathway of the metabolic pathways. For instance, if the analytics system 100 determines that a given metabolic pathway is not indicative of (e.g., strongly correlated to) an expected agronomic attribute, the analytics system 100 determines not to use that given metabolic pathway in the determination of the measure of the agronomic attribute.

In an optional step 860, the soil at the geographical location may be treated according to the measure of the agronomic attribute. For example, an amount of fertilizer supplied to the soil may be increased or decreased based on the nitrogen mineralization metric for the soil. In some embodiments, the analytics system 100 can determine a recommendation for treatment of the soil using at least the measure of the agronomic attribute. The analytics system 100 may also transmit the measure of the agronomic attribute to a client device for display to a user. The analytics system 100 may calculate a community percentile metric of the measure of the agronomic attribute using reference metrics.

IV. Example Metrics

FIGS. 3-6 illustrate utility of the methods described herein. For example, the soil health indicator results reveal useful correlations between counts of certain functional genes and characteristics of soil. The analytics system 100 may determine specific recommendations (e.g., for treating soil) using these correlations.

A. Nitrogen Cycling

Figure 3:
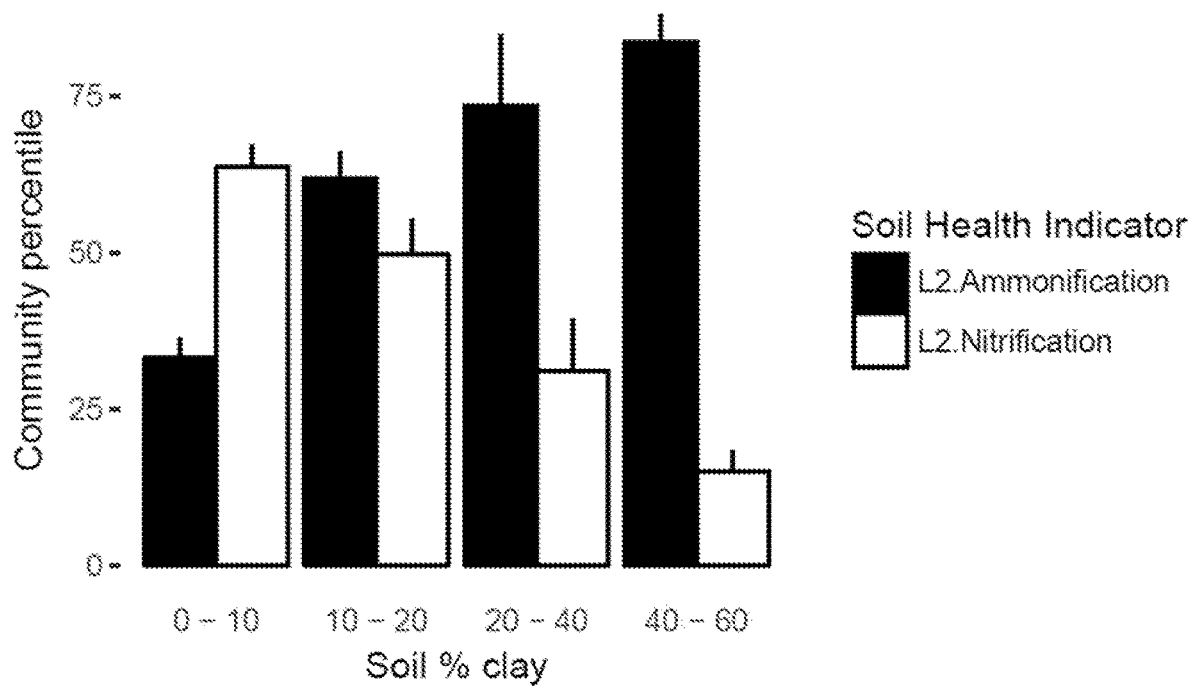
FIG. 3 illustrates example nitrogen cycling soil health indicators according to an embodiment.

FIG. 3 illustrates example nitrogen cycling soil health indicators according to an embodiment. FIG. 3 shows variation in community percentile abundance of the gene count based nitrogen cycling SHIs "L2.Ammonification" and "L2.Nitrificaiton" with soil clay content across 108 agricultural soils. SHI data is derived from calculations based on functional gene counts obtained from DNA extracted from each soil, and error bars are +1 SE.

Figure 6:
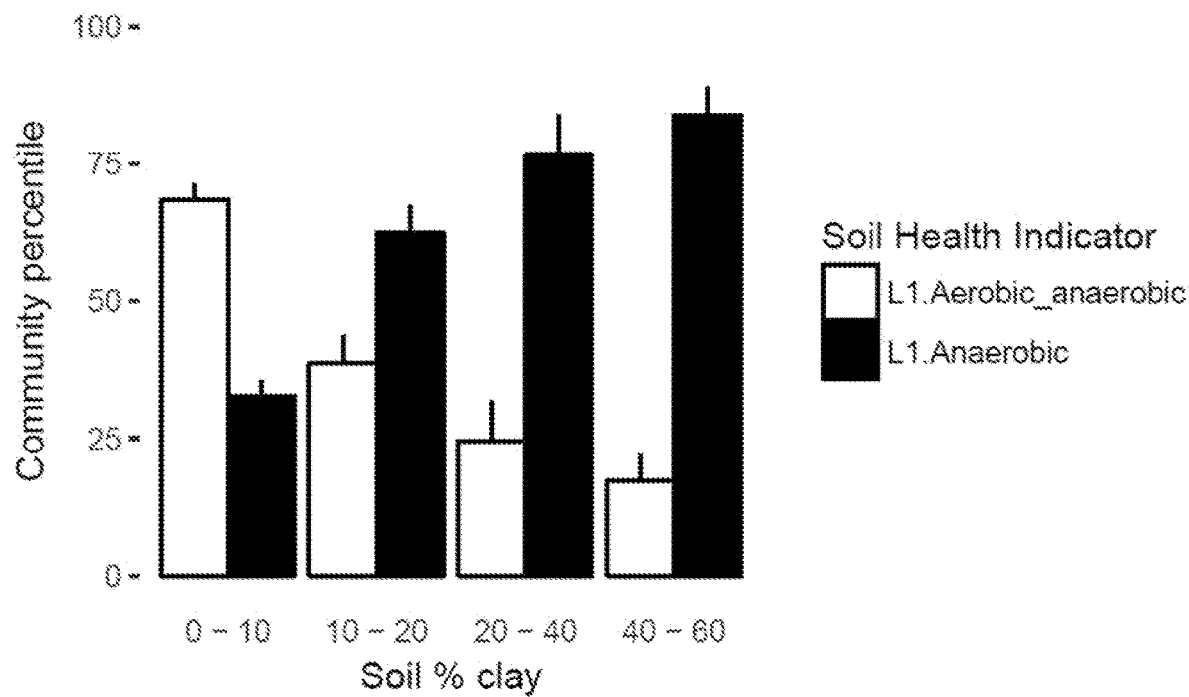
FIG. 6 illustrates example oxygen availability soil health indicators according to an embodiment.

FIG. 3 indicates that soil clay content may be inversely related to drainage and oxygen availability. Therefore, higher clay content soils are expected to be less aerobic (e.g., as shown in FIG. 6). Ammonification is the microbial reductive process (e.g., removing an electron or oxygen atom), which converts inorganic nitrate to ammonium. Abundance of ammonification genes in lower clay soils may result from lower oxygen availability in these soils. Nitrification is the reverse process of converting ammonium to nitrate, which requires oxygen. Greater abundance of nitrification genes in lower clay content soils may in part reflect their higher oxygen availability. Both of these microbial processes may have implications for soil nitrogen cycling and agricultural fertility.

Ammonification is the process of converting inorganic nitrate ($NO_3^-$) to ammonium ($NH_4^+$), which is free outside the cell. This process is also known as dissimilatory nitrate reduction or DNRA. In agricultural soils, this microbial process may help stem the loss of inorganic nitrogen by solubilization and leaching, as $NO_3^-$ is soluble in soil solution whereas $NH_4^+$ is not (due to differences in polarity and ionic adsorption). Thus, ammonification may help stop the loss of nitrate by converting it to ammonium. Greater abundance of ammonification genes in these clay soils may reflect greater N retention.

Nitrification is the process of converting ammonium or ammonia ($NH_4^+$ or $NH_3$) to nitrate ($NO_3^-$), which may be further divided by different bacterial groups carrying out conversions between $NH_4^+/NH_3 \rightarrow NO_2^-$ and then $NO_2^- \rightarrow NO_3^-$. In agricultural settings, many N fertilizers may be applied as forms of $NH_4^+$ to reduce their mobility and leaching. Nitrifying bacteria can convert this $NH_4^+/NH_3$ into the readily soluble $NO_3^-$. While both $NH_4^+/NH_3$ and $NO_3^-$ are available for uptake by plant roots, $NO_3^-$ may be lost either to leaching or to the atmosphere as $N_2$ as the product of denitrifying bacterial respiration. Thus, nitrification represents a conversion to forms of N that are potentially lost in agricultural soils, and the potential for this process may be greater in soils with less clay content.

B. Phosphorous Cycling

Figure 4:
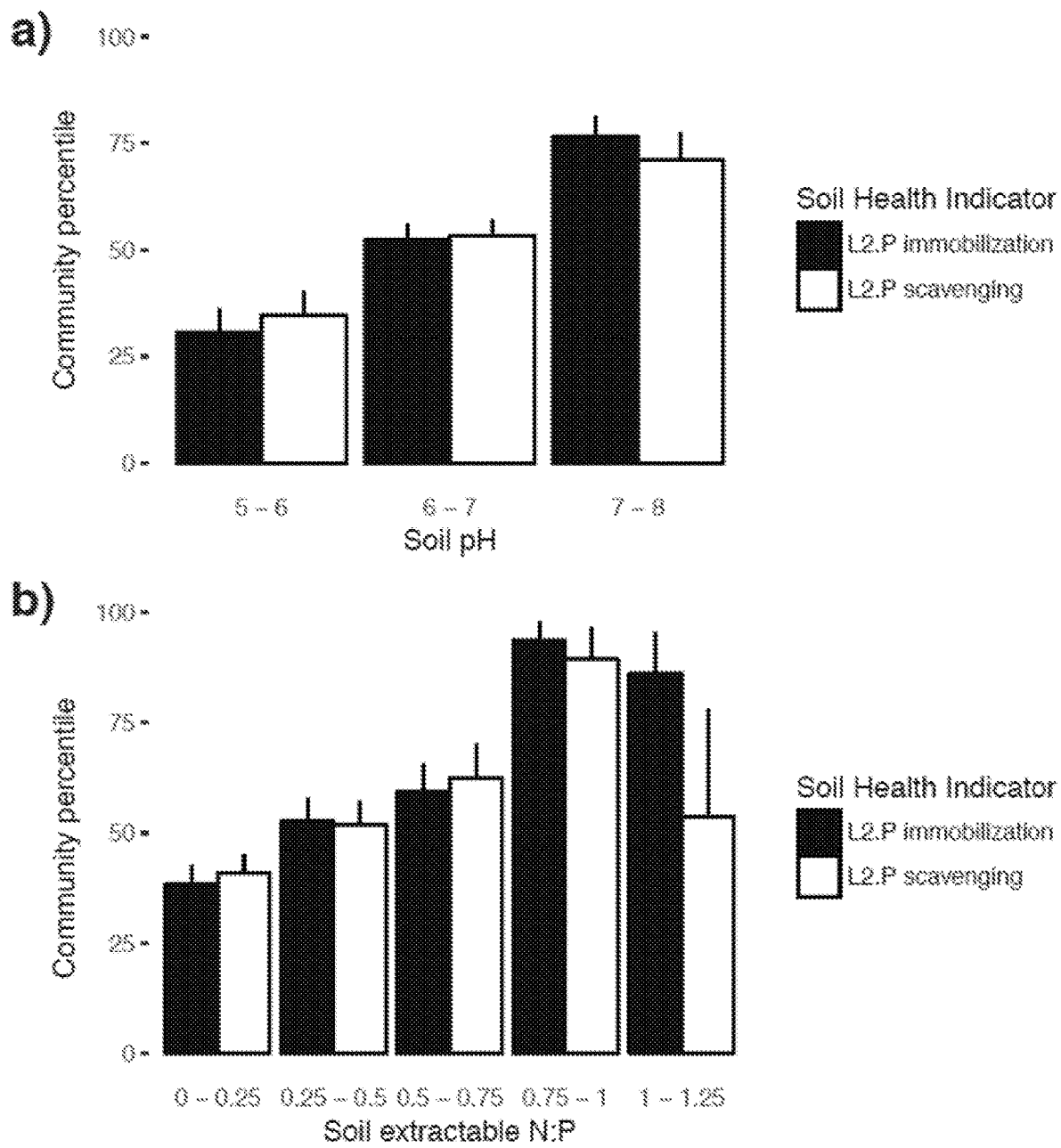
FIG. 4 illustrates example phosphorous cycling soil health indicators according to an embodiment.

FIG. 4 illustrates example phosphorous cycling soil health indicators according to an embodiment. FIG. 4 shows variation in community percentile abundance of the gene count based phosphorus cycling SHIs "L2.P immobilization" and "L2.P scavenging" with a) soil pH content, and b) soil extractable nitrogen to phosphorus ratios across 108 agricultural soils. SHI data is derived from calculations based on functional gene counts obtained from DNA extracted from each soil, and error bars are +1 SE.

Soil P immobilization (uptake into microbial biomass, here inorganic P transporter genes) and Soil P scavenging (SHI level 2 includes mineral P solubilization, phosphatase and phosphonate lysis genes, described in Table 2) are two opposing processes. The first represents incorporation of inorganic P into microbial cells, while the second represents the potential to produce inorganic P from soil organic matter or mineral forms in the case of P solubilization.

However, the abundance of each of these gene categories may commonly reflect microbial effort allocated to acquire P, either by incorporating it or liberating it into solution. Thus, while metabolic functions differ between P solubilization and P scavenging, they may display common patterns along soil gradients.

Increasing microbial allocation to P acquisition via both P immobilization and P solubilization with soil pH (panel a) likely reflects pH driven changes in soil P availability. Soil pH affects the solubility and oxidation state of soil metals, which adsorb inorganic P (phosphate or $PO_4^-$). More acidic soils have more reduced metals including iron and aluminum, which in turn have less ability to adsorb inorganic P. Therefore, P availability is expected to be higher in acidic soils (lower pH), and lower in more basic soils (higher pH). The panel a) shows P acquisition gene SHIs (including P immobilization and P solubilization) increase with soil pH, and presumably therefore with P limitation.

P limitation may be assessed by comparing its relative availability, often when compared to N as indicated by N:P ratios. As N:P ratios increase, the relative availability of P decreases, reflecting declining P availability. Panel b) shows that microbial P acquisition gene abundances increase with increasing soil extractable N:P, a proxy for P limitation. Critical N:P ratios for plants and soils commonly are commonly divided as: N limited <N:P=16:1>P limited. However, soil extractable N:P (more direct measure of inorganic nutrient availability) tends to align with a different scale described by "ecoenzymatic stoichiometry" where the ratio of enzymes for transforming these elements in balance is at N:P=1:1.

C. Carbon Cycling

Figure 5:
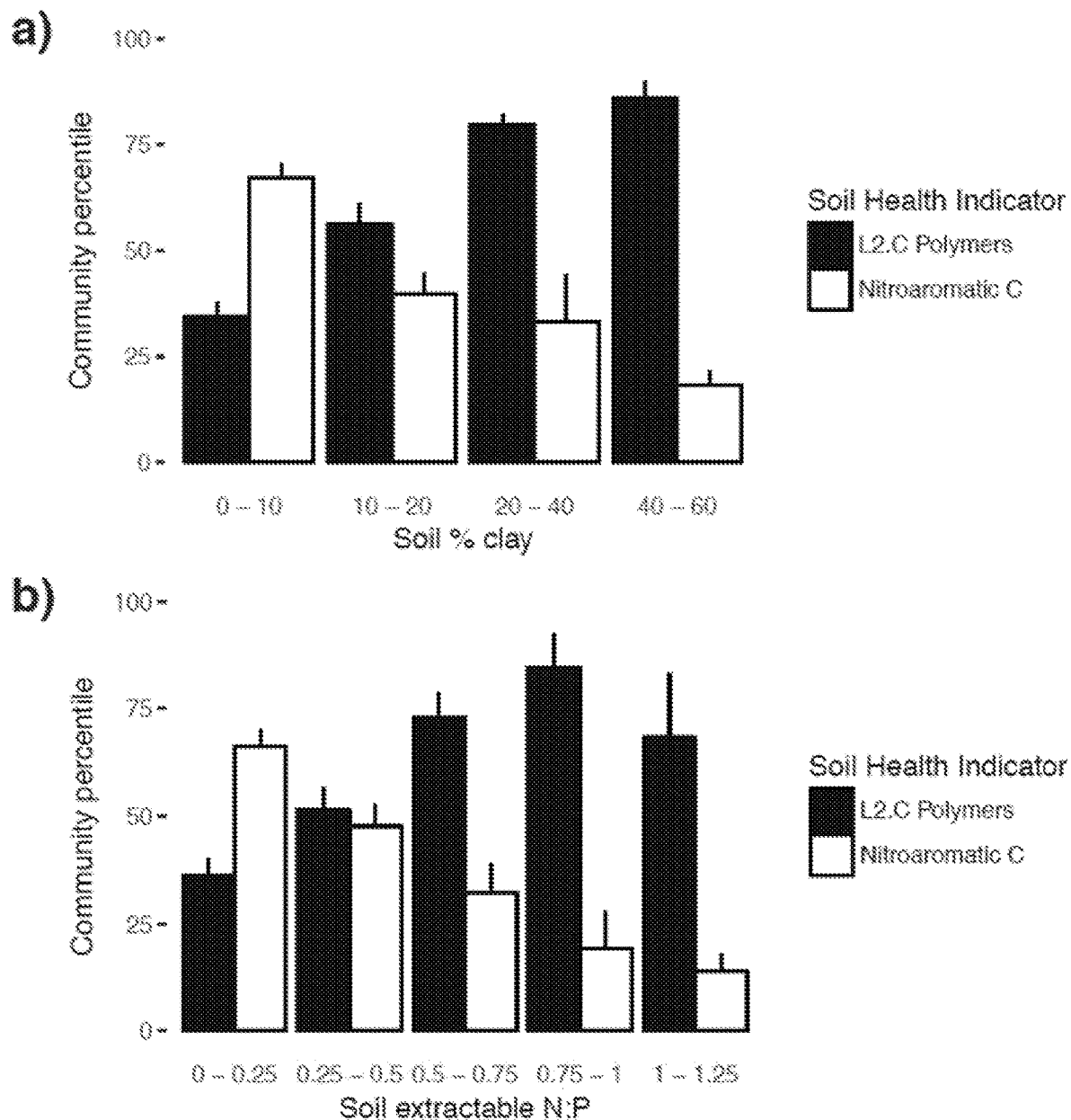
FIG. 5 illustrates example carbon cycling soil health indicators according to an embodiment.

FIG. 5 illustrates example carbon cycling soil health indicators according to an embodiment. FIG. 5 shows variation in community percentile abundance of the gene count based carbon cycling SHIs "L2.0 Polymers" and "Nitroaromatics C" compounds with a) soil clay content, and b) soil extractable nitrogen to phosphorus ratios across 108 agricultural soils. SHI data is derived from calculations based on functional gene counts obtained from DNA extracted from each soil, and error bars are +1 SE.

As shown in panel a), community percentiles of SHI level 2 category "L2.0 Polymers" increase with soil clay content. The level 2 Polymers SHI category includes genes for the degradation of most plant biomass constituents (see Tables 1, 5). These polymers are known to bind to soil clay minerals, and higher gene abundances for their degradation reflects greater microbial allocation to access them in clay soils where they are more tightly bound.

In an opposite trend, genes grouped under the Nitroaromatics class ("C_arom_nitro") decreased with soil clay content. These genes degrade nitroaromatic compounds, which could reflect scavenging of organic matter for nitrogen under limiting conditions. One interpretation of the decrease nitroaromatic degrading genes with increasing clay might be that low clay soils are more likely to be sandy, and sandy soils are known to be nitrogen poor. Higher abundances of nitroaromatic degrading genes in these soils would reflect increased nitrogen scavenging from aromatics in these lower nitrogen soils.

As shown in panel b), the community percentile abundance of genes degrading nitroaromatics decreased with increasing ratios of soil extractable nitrogen:phosphorus (Extractable N:P). As this ratio increases, nitrogen becomes increasingly available relative to phosphorus, such that higher numbers reflect decreasing nitrogen limitation. Decreasing nitroaromatic degrading genes with extractable N:P likely reflect lesser allocation to organic N scavenging from C compounds as N is more readily available at higher N:P. Extractable N:P ratios may better reflect the availability of inorganic forms of these elements when compared to total soil N:P.

Higher abundance of polymer degrading genes with increasing soil N:P may be in part attributable to the association of accumulated soil organic matter with both nitrogen content and ionic adsorption of ammonium.

D. Oxygen Availability

FIG. 6 illustrates example oxygen availability soil health indicators according to an embodiment. FIG. 6 shows variation in community percentile abundance of the gene count based oxygen availability SHIs "L1.Aerobic_anaerobic" and "L1.Anaerobic" with soil clay content across 108 agricultural soils. The latter represents scaled counts of genes involved in microbial anaerobic respiration while the former is the ratio of aerobic to anaerobic respiration genes. SHI data is derived from calculations based on functional gene counts obtained from DNA extracted from each soil, and error bars are +1 SE.

FIG. 6 indicates that soil clay content may be inversely related to drainage and oxygen availability. Therefore, higher clay content soils are expected to be less aerobic. FIG. 6 shows that the proportion of genes for aerobic respiration increases relative to those for anaerobic metabolism as clay content increases. Increasing clay content may also be directly related to higher relative abundances of genes for anaerobic respiration.

V. Additional Considerations

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

VI. Tables of Individual Genes Used to Calculate Soil Health Indicators

A. Nitrogen Cycling

TABLE 5

Table 5: List of genes, gene identifiers, and metabolic pathways and classes used for soil health indicators for agricultural nitrogen cycling. Gene counts matching each identifier are obtained from soil DNA sequencing and gene annotation tools. Indicators can be formulated as normalized counts of these indicators, ratios, weighted sums, etc. Here, gene IDs represent identifiers for these genes in either the KEGG ontology or the Pfam protein database, while EC numbers are Enzyme commission identifiers.

| Class | Pathway | Gene ID | Gene name | Gene function | EC |
|---|---|---|---|---|---|
| N_fixation | N2_fix | K02588 | nifH | nitrogenase iron protein NifH | [EC: 1.18.6.1] |
| N_fixation | N2_fix | K02586 | nifD | nitrogenase molybdenum-iron protein alpha chain | [EC: 1.18.6.1] |
| N_fixation | N2_fix | K02591 | nifK | nitrogenase molybdenum-iron protein beta chain | [EC: 1.18.6.1] |
| N_fixation | N2_fix | K02595 | nifW | nitrogenase-stabilizing/protective protein | |
| N_fixation | N2_fix | K00531 | anfG | nitrogenase delta subunit | [EC: 1.18.6.1] |
| Denitrification | N_DNT | K00368 | nirK | nitrite reductase (NO-forming) | [EC: 1.7.2.1] |
| Denitrification | N_DNT | K15864 | nirS | nitrite reductase (NO-forming)/hydroxylamine reductase | [EC: 1.7.2.1 1.7.99.1] |
| Denitrification | N_DNT | K04561 | norB | nitric oxide reductase subunit B | [EC: 1.7.2.5] |
| Denitrification | N_DNT | K02305 | norC | nitric oxide reductase subunit C | NA |
| Denitrification | N_DNT | K15877 | CYP55 | fungal nitric oxide reductase | [EC: 1.7.1.14] |
| Denitrification | N_DNT | K00376 | nosZ | nitrous-oxide reductase | [EC: 1.7.2.4] |
| Ammonification | NO3_D_red | K03385 | nrfA | nitrite reductase (cytochrome c-5 | [EC: 1.7.2.2] |
| Ammonification | NO3_D_red | K04013 | nrfB | cytochrome c-type protein NrfB | |
| Ammonification | NO3_D_red | K04014 | nrfC | protein NrfC | |
| Ammonification | NO3_D_red | K04015 | nrfD | protein NrfD | |
| Ammonification | NO3_D_red | K15876 | nrfH | cytochrome c nitrite reductase small subunit | NA |
| Nitrification | NH3_oxid | K10944 | pmoA-amoA | methane/ammonia monooxygenase subunit A | [EC: 1.14.18.3 1.14.99.39] |
| Nitrification | NH3_oxid | K10945 | pmoB-amoB | methane/ammonia monooxygenase subunit B | NA |
| Nitrification | NH3_oxid | K10946 | pmoC-amoC | methane/ammonia monooxygenase subunit C | NA |
| Nitrification | NH3_oxid | K10535 | hao | hydroxylamine dehydrogenase | [EC: 1.7.2.6] |
| Immobilization | NO3_transp | K02575 | NRT, narK, nrtP, nasA | MFS transporter, NNP family, nitrate/nitrite transporter | [tc: 2.A.1.8] |
| Immobilization | NO3_transp | K10850 | narT | MFS transporter, NNP family, putative nitrate transporter | [tc: 2.A.1.8] |
| Immobilization | NO3_A_red | K10534 | NR | nitrate reductase (NAD(P)H) | [EC: 1.7.1.1 1.7.1.2 1.7.1.3] |
| Immobilization | NO3_A_red | K00360 | nasB | assimilatory nitrate reductase electron transfer subunit | [EC: 1.7.99.4] |
| Immobilization | NO3_A_red | K00366 | nirA | ferredoxin-nitrite reductase | [EC: 1.7.7.1] |

TABLE 5-continued

Table 5: List of genes, gene identifiers, and metabolic pathways and classes used for soil health indicators for agricultural nitrogen cycling. Gene counts matching each identifier are obtained from soil DNA sequencing and gene annotation tools. Indicators can be formulated as normalized counts of these indicators, ratios, weighted sums, etc. Here, gene IDs represent identifiers for these genes in either the KEGG ontology or the Pfam protein database, while EC numbers are Enzyme commission identifiers.

| Class | Pathway | Gene ID | Gene name | Gene function | EC |
|---|---|---|---|---|---|
| Immobilization | NH4_asim | K00260 | gudB, rocG | glutamate dehydrogenase | [EC: 1.4.1.2] |
| Immobilization | NH4_asim | K00261 | gdhA | glutamate dehydrogenase (NAD(P)+) | [EC: 1.4.1.3] |
| Immobilization | NH4_asim | K00262 | gdhA | glutamate dehydrogenase (NADP+) | [EC: 1.4.1.4] |
| Immobilization | NH4_asim | K00264 | GLT1 | glutamate synthase (NADPH/NADH) | [EC: 1.4.1.13 1.4.1.14] |
| Immobilization | NH4_asim | K00265 | gltB | glutamate synthase (NADPH/NADH) large chain | [EC: 1.4.1.13 1.4.1.14] |
| Immobilization | NH4_asim | K00266 | gltD | glutamate synthase (NADPH/NADH) small chain | [EC: 1.4.1.13 1.4.1.14] |
| Immobilization | NH4_asim | K00284 | GLU2 | glutamate synthase (ferredoxin) | [EC: 1.4.7.1] |
| Immobilization | NH4_asim | K01425 | glsA, GLS | glutaminase | [EC: 3.5.1.2] |
| Immobilization | NH4_asim | K01915 | glnA, GLUL | glutamine synthetase | [EC: 6.3.1.2] |
| Immobilization | NH4_asim | K01953 | asnB, ASNS | asparagine synthase (glutamine-hydrolysing) | [EC: 6.3.5.4] |
| Immobilization | NH4_asim | K05597 | aspQ, ansB, ansA | glutamin-(asparagin-)ase | [EC: 3.5.1.38] |
| Immobilization | NH4_asim | K15371 | GDH2 | glutamate dehydrogenase | [EC: 1.4.1.2] |
| Mineralization | Urea_min | K01427 | URE | urease | [EC: 3.5.1.5] |
| Mineralization | Urea_min | K01428 | ureC | urease subunit alpha | [EC: 3.5.1.5] |
| Mineralization | Urea_min | K01429 | ureB | urease subunit beta | [EC: 3.5.1.5] |
| Mineralization | Urea_min | K01430 | ureA | urease subunit gamma | [EC: 3.5.1.5] |
| Mineralization | Urea_transp | K11959 | urtA | urea transport system substrate-binding protein | NA |
| Mineralization | Urea_transp | K11960 | urtB | urea transport system permease protein | NA |
| Mineralization | Urea_transp | K11961 | urtC | urea transport system permease protein | NA |
| Mineralization | Urea_transp | K11962 | urtD | urea transport system ATP-binding protein | NA |
| Mineralization | Urea_transp | K11963 | urtE | urea transport system ATP-binding protein | NA |
| Mineralization | Chitinases | K01183 | E3.2.1.14 | chitinase | [EC: 3.2.1.14] |
| Mineralization | Chitinases | K01207 | nagZ | beta-N-acetylhexosaminidase | [EC: 3.2.1.52] |
| Mineralization | Chitinases | K01212 | sacC | levanase | [EC: 3.2.1.65] |
| Mineralization | Chitinases | K01233 | csn | chitosanase | [EC: 3.2.1.132] |
| Mineralization | Chitinases | K01452 | E3.5.1.41 | chitin deacetylase | [EC: 3.5.1.41] |
| Mineralization | Chitinases | K12373 | HEXA_B | hexosaminidase | [EC: 3.2.1.52] |
| Mineralization | Chitinases | K13381 | chiA | bifunctional chitinase/lysozyme | [EC: 3.2.1.14 3.2.1.17] |
| Mineralization | Chitinases | K14459 | HEX | hexosaminidase | [EC: 3.2.1.52] |
| Mineralization | Secreted_proteases | PF02560 | cynS | cyanate lyase | [EC: 4.2.1.104] |
| Mineralization | Secreted_proteases | PF08548 | aprA | serralysin | [EC: 3.4.24.40] |
| Mineralization | Secreted_proteases | PF01447 | nprS | thermalysin | [EC: 3.4.24.40] |
| Mineralization | Secreted_proteases | PF02868 | nprS | thermalysin | [EC: 3.4.24.40] |
| Ambig_NO3r | a_NO3_D_red | K00362 | nirB | nitrite reductase (NADH) large subunit | [EC: 1.7.1.15] |
| Ambig_NO3r | a_NO3_D_red | K00363 | nirD | nitrite reductase (NADH) small subunit | [EC: 1.7.1.15] |

TABLE 5-continued

Table 5: List of genes, gene identifiers, and metabolic pathways and classes used for soil health indicators for agricultural nitrogen cycling. Gene counts matching each identifier are obtained from soil DNA sequencing and gene annotation tools. Indicators can be formulated as normalized counts of these indicators, ratios, weighted sums, etc. Here, gene IDs represent identifiers for these genes in either the KEGG ontology or the Pfam protein database, while EC numbers are Enzyme commission identifiers.

| Class | Pathway | Gene ID | Gene name | Gene function | EC |
|---|---|---|---|---|---|
| Ambig_NO3r | a_N_DNT | K00370 | narG, narZ, nxrA | nitrate reductase/nitrite oxidoreductase, alpha subunit | [EC: 1.7.5.1 1.7.99.4] |
| Ambig_NO3r | a_NO3_red | K00371 | narH, narY, nxrB | nitrate reductase/nitrite oxidoreductase, beta subunit | [EC: 1.7.5.1 1.7.99.4] |
| Ambig_NO3r | a_NO3_red | K00374 | narI, narV | nitrate reductase gamma subunit | [EC: 1.7.5.1 1.7.99.4] |
| Ambig_NO3r | a_NO3_red | K00373 | narJ, narW | nitrate reductase delta subunit | NA |
| Ambig_NO3r | a_NO3_red | K02567 | napA | periplasmic nitrate reductase NapA | [EC: 1.7.99.4] |
| Ambig_NO3r | a_NO3_red | K02568 | napB | cytochrome c-type protein NapB | NA |
| Ambig_NO3r | a_NO3_A_red | K00372 | nasA | assimilatory nitrate reductase catalytic subunit | [EC: 1.7.99.4] |
| Ambig_NO3r | a_NO3_red | K15878 | narB | rieske iron-sulfur protein | NA |
| Ambig_NO3r | a_NO3_red | K15879 | narC | cytochrome b-561 | NA |

B. Phosphorus Cycling

TABLE 6

Table 6: List of genes, gene identifiers, and metabolic pathways and classes used for soil health indicators for agricultural phosphorus cycling. Gene counts matching each identifier are obtained from soil DNA sequencing and gene annotation tools. Indicators can be formulated as normalized counts of these indicators, ratios, weighted sums, etc. Here, gene IDs represent identifiers for these genes in either the KEGG ontology or the Pfam protein database, while EC numbers are Enzyme Commission identifiers, or corresponding transporter identifiers (if TC:).

| Class | Pathway | Gene ID | Gene name | Gene function | EC |
|---|---|---|---|---|---|
| P_immobil | P_transp | K02040 | pstS | phosphate transport system substrate-binding protein | [TC: 3.A.1.7.1] |
| P_immobil | P_transp | K02037 | pstC | phosphate transport system permease protein | [TC: 3.A.1.7.1] |
| P_immobil | P_transp | K02038 | pstA | phosphate transport system permease protein | [TC: 3.A.1.7.1] |
| P_immobil | P_transp | K02036 | pstB | phosphate transport system ATP-binding protein | [EC: 3.6.3.27] |
| P_immobil | P_transp | PF02690 | yjbB | phosphate: Na+ symporter | [TC: 2.A.58.2] |
| P_immobil | P_transp | PF01384 | pit | inorganic phosphate transporter, PiT family | [TC: 2.A.20] |
| P_immobil | P_transp | PF01384 | pitA | low-affinity inorganic phosphate transporter | [TC: 2.A.20.1] |
| P_immobil | P_transp | PF07396 | oprO_P | phosphate-selective porin OprO and OprP | [TC: 1.B.5.1] |
| Polyphosphate | Inorg_Pase | PF02503 | ppk | polyphosphate kinase | [EC: 2.7.4.1] |
| Polyphosphate | Inorg_Pase | PF13090 | ppk | polyphosphate kinase | [EC: 2.7.4.1] |
| Polyphosphate | Inorg_Pase | PF13089 | ppk | polyphosphate kinase | [EC: 2.7.4.1] |

TABLE 6-continued

Table 6: List of genes, gene identifiers, and metabolic pathways and classes used for soil health indicators for agricultural phosphorus cycling. Gene counts matching each identifier are obtained from soil DNA sequencing and gene annotation tools. Indicators can be formulated as normalized counts of these indicators, ratios, weighted sums, etc. Here, gene IDs represent identifiers for these genes in either the KEGG ontology or the Pfam protein database, while EC numbers are Enzyme Commission identifiers, or corresponding transporter identifiers (if TC:).

| Class | Pathway | Gene ID | Gene name | Gene function | EC |
|---|---|---|---|---|---|
| P_scavenging | Inorg_Pase | K01507 | ppa | inorganic pyrophosphatase | NA |
| P_scavenging | Inorg_Pase | K15986 | ppaC | manganese-dependent inorganic pyrophosphatase | NA |
| P_scavenging | Inorg_Pase | K01514 | PRUNE, PPX1 | exopolyphosphatase | [EC: 3.6.1.11] |
| P_scavenging | Inorg_Pase | K01524 | ppx-gPPA | exopolyphosphatase/ guanosine-5'-triphosphate,3'-diphosphate pyrophosphatase | [EC: 3.6.1.11 3.6.1.40] |
| P_scavenging | P_solubil | PF08042 | pqqA | pyrroloquinoline quinone biosynthesis protein A | [EC: 1.3.3.11] |
| P_scavenging | P_solubil | PF05402 | pqqD | pyrroloquinoline quinone biosynthesis protein D | [EC: 1.3.3.11] |
| P_scavenging | P_solubil | PF00311 | ppc | phosphoenolpyruvate carboxylase | [EC: 4.1.1.31] |
| P_scavenging | P_solubil | PF16912 | gdh | glucose/galactose 1-dehydrogenase (NADP+) | [EC: 1.1.1.360] |
| P_scavenging | Glyc_3_pase | K05814 | ugpA | Glycerol-3-phosphate transporter subunit ugpA | NA |
| P_scavenging | Glyc_3_pase | K05813 | ugpB | Glycerol-3-phosphate transporter subunit ugpB | NA |
| P_scavenging | Glyc_3_pase | K05816 | ugpC | Glycerol-3-phosphate transporter subunit ugpC | [EC: 3.6.3.20] |
| P_scavenging | Glyc_3_pase | K05815 | ugpE | Glycerol-3-phosphate transporter subunit ugpE | NA |
| P_scavenging | P_ases | PF03767 | aphA | Acid phosphatase aphaA | [EC: 3.1.3.2] |
| P_scavenging | P_ases | PF00245 | phoA, phoB, phoX | alkaline phosphatase | [EC: 3.1.3.1] |
| P_scavenging | P_ases | PF02333 | phyC | 3-phytase | [EC: 3.1.3.8] |
| P_scavenging | P_ases | PF00328 | appA | 4-phytase/acid phosphatase | [EC: 3.1.3.26 3.1.3.2] |
| P_scavenging | phn_transp | K02044 | phnD | phosphonate transport system substrate-binding protein | NA |
| P_scavenging | phn_transp | K02042 | phnE | phosphonate transport system permease protein | NA |
| P_scavenging | phn_transp | K02041 | phnC | phosphonate transport system ATP-binding protein | [EC: 3.6.3.28] |
| P_scavenging | phn_transp | K11081 | phnS | 2-aminoethylphosphonate transport system substrate-binding protein | NA |

TABLE 6-continued

Table 6: List of genes, gene identifiers, and metabolic pathways and classes used for soil health indicators for agricultural phosphorus cycling. Gene counts matching each identifier are obtained from soil DNA sequencing and gene annotation tools. Indicators can be formulated as normalized counts of these indicators, ratios, weighted sums, etc. Here, gene IDs represent identifiers for these genes in either the KEGG ontology or the Pfam protein database, while EC numbers are Enzyme Commission identifiers, or corresponding transporter identifiers (if TC:).

| Class | Pathway | Gene ID | Gene name | Gene function | EC |
|---|---|---|---|---|---|
| P_scavenging | phn_transp | K11082 | phnV | 2-aminoethylphosphonate transport system permease protein | NA |
| P_scavenging | phn_transp | K11083 | phnU | 2-aminoethylphosphonate transport system permease protein | NA |
| P_scavenging | phn_transp | K11084 | phnT | 2-aminoethylphosphonate transport system ATP-binding protein | NA |
| P_scavenging | phn_transp | K05781 | phnK | C-P lyase multienzyme complex phnK | NA |
| P_scavenging | phn_transp | K05780 | phnL | C-P lyase multienzyme complex phnL | NA |
| P_scavenging | phn_degrad | K09994 | phnO | C-P lyase multienzyme complex phnO | [EC: 2.3.1.—] |
| P_scavenging | phn_degrad | PF03831 | phnA | phosphonoacetate hydrolase | [EC: 3.11.1.2] |
| P_scavenging | phn_degrad | PF05861 | phnI | alpha-D-ribose 1-methylphosphonate 5-triphosphate synthase subunit PhnI | [EC: 2.7.8.37] |
| P_scavenging | phn_degrad | PF06754 | phnG | alpha-D-ribose 1-methylphosphonate 5-triphosphate synthase subunit PhnG | [EC: 2.7.8.37] |
| P_scavenging | phn_degrad | PF05845 | phnH | alpha-D-ribose 1-methylphosphonate 5-triphosphate synthase subunit PhnH | [EC: 2.7.8.37] |
| P_scavenging | phn_degrad | K05780 | phnL | alpha-D-ribose 1-methylphosphonate 5-triphosphate synthase subunit PhnL | [EC: 2.7.8.37] |
| P_scavenging | phn_degrad | PF06007 | phnJ | alpha-D-ribose 1-methylphosphonate 5-phosphate C-P lyase | [EC: 4.7.1.1] |

C. Carbon Cycling

TABLE 7

Table 7: List of genes, gene identifiers, and metabolic pathways and classes used for soil health indicators for agricultural carbon cycling. Gene counts matching each identifier are obtained from soil DNA sequencing and gene annotation tools. Indicators can be formulated as normalized counts of these indicators, ratios, weighted sums, etc. Here, gene IDs represent identifiers for these genes in the KEGG ontology, while EC numbers are Enzyme Commission identifiers.

| Carbon class | Compound | Gene ID | Gene name | Gene function | EC |
|---|---|---|---|---|---|
| Sugars | C_sug_sucr | K00847 | scrK | fructokinase | [EC: 2.7.1.4] |
| Sugars | C_sug_sucr | K00012 | UGDH, ugd | UDPglucose 6-dehydrogenase | [EC: 1.1.1.22] |

TABLE 7-continued

Table 7: List of genes, gene identifiers, and metabolic pathways and classes used for soil health indicators for agricultural carbon cycling. Gene counts matching each identifier are obtained from soil DNA sequencing and gene annotation tools. Indicators can be formulated as normalized counts of these indicators, ratios, weighted sums, etc. Here, gene IDs represent identifiers for these genes in the KEGG ontology, while EC numbers are Enzyme Commission identifiers.

| Carbon class | Compound | Gene ID | Gene name | Gene function | EC |
|---|---|---|---|---|---|
| Sugars | C_sug_sucr | K12447 | USP | UDP-sugar pyrophosphorylase | [EC: 2.7.7.64] |
| Sugars | C_sug_sucr | K06859 | pgi1 | glucose-6-phosphate isomerase, archaeal | [EC: 5.3.1.9] |
| Sugars | C_sug_sucr | K01835 | pgm | phosphoglucomutase | [EC: 5.4.2.2] |
| Sugars | C_sug_sucr | K01810 | GPI, pgi | glucose-6-phosphate isomerase | [EC: 5.3.1.9] |
| Sugars | C_sug_sucr | K00846 | KHK | ketohexokinase | [EC: 2.7.1.3] |
| Sugars | C_sug_sucr | K04041 | fbp3 | fructose-1,6-bisphosphatase III | [EC: 3.1.3.11] |
| Sugars | C_sug_sucr | K01623 | ALDO | fructose-bisphosphate aldolase, class I | [EC: 4.1.2.13] |
| Sugars | C_sug_sucr | K11645 | fbaB | fructose-bisphosphate aldolase, class I | [EC: 4.1.2.13] |
| Sugars | C_sug_sucr | K01624 | FBA, fbaA | fructose-bisphosphate aldolase, class II | [EC: 4.1.2.13] |
| Sugars | C_sug_lact | K12308 | bgaB, lacA | beta-galactosidase | [EC: 3.2.1.23] |
| Sugars | C_sug_lact | K01819 | lacA, lacB | galactose-6-phosphate isomerase | [EC: 5.3.1.26] |
| Sugars | C_sug_lact | K00917 | lacC | tagatose 6-phosphate kinase | [EC: 2.7.1.144] |
| Sugars | C_sug_lact | K01635 | lacD | tagatose 1,6-diphosphate aldolase | [EC: 4.1.2.40] |
| Sugars | C_sug_lact | K01190 | lacZ | beta-galactosidase | [EC: 3.2.1.23] |
| Sugars | C_sug_gal | K01785 | galM, GALM | aldose 1-epimerase | [EC: 5.1.3.3] |
| Sugars | C_sug_gal | K00849 | galK | galactokinase | [EC: 2.7.1.6] |
| Sugars | C_sug_gal | K00965 | galT, GALT | UDPglucose--hexose-1-phosphate uridylyltransferase | [EC: 2.7.7.12] |
| Sugars | C_sug_gal | K01784 | galE, GALE | UDP-glucose 4-epimerase | [EC: 5.1.3.2] |
| Sugars | C_sug_gal | K01835 | pgm | phosphoglucomutase | [EC: 5.4.2.2] |
| Sugars | C_sug_gal | K00035 | gal | D-galactose 1-dehydrogenase | [EC: 1.1.1.48] |
| Sugars | C_sug_treh | K01194 | treA, treF | alpha, alpha-trehalase | [EC: 3.2.1.28] |
| Sugars | C_sug_treh | K01226 | treC | trehalose-6-phosphate hydrolase | [EC: 3.2.1.93] |
| Sugars | C_sug_treh | K00845 | glk | glucokinase | [EC: 2.7.1.2] |
| Sugars | C_sug_rham | K01820 | rhaA | L-rhamnose isomerase/sugar isomerase | [EC: 5.3.1.14, 5.3.1.—] |
| Sugars | C_sug_rham | K00848 | rhaB | rhamnulokinase | [EC: 2.7.1.5] |
| Sugars | C_sug_rham | K01629 | rhaD | rhamnulose-1-phosphate aldolase | [EC: 4.1.2.19] |
| Sugars | C_sug_rham | K18337 | LRA1 | L-rhamnose 1-dehydrogenase | [EC: 1.1.1.173] |
| Sugars | C_sug_rham | K18338 | LRA2 | L-rhamnono-1,4-lactonase | [EC: 3.1.1.65] |
| Sugars | C_sug_rham | K12661 | LRA3, yfaW | L-rhamnonate dehydratase | [EC: 4.2.1.90] |
| Sugars | C_sug_rham | K18339 | LRA4 | 2-keto-3-deoxy-L-rhamnonate aldolase | [EC: 4.1.2.53] |

TABLE 7-continued

Table 7: List of genes, gene identifiers, and metabolic pathways and classes used for soil health indicators for agricultural carbon cycling. Gene counts matching each identifier are obtained from soil DNA sequencing and gene annotation tools. Indicators can be formulated as normalized counts of these indicators, ratios, weighted sums, etc. Here, gene IDs represent identifiers for these genes in the KEGG ontology, while EC numbers are Enzyme Commission identifiers.

| Carbon class | Compound | Gene ID | Gene name | Gene function | EC |
|---|---|---|---|---|---|
| Sugars | C_sug_rham | K01813 | rhaA | L-rhamnose isomerase | [EC: 5.3.1.14] |
| Sugars | C_sug_arab | K05305 | FUK | fucokinase | [EC: 2.7.1.52] |
| Sugars | C_sug_arab | K01818 | fucI | L-fucose isomerase | [EC: 5.3.1.25] |
| Sugars | C_sug_arab | K00879 | fucK | L-fuculokinase | [EC: 2.7.1.51] |
| Sugars | C_sug_arab | K01628 | fucA | L-fuculose-phosphate aldolase | [EC: 4.1.2.17] |
| Sugars | C_sug_arab | K18334 | fucD | L-fuconate dehydratase | [EC: 4.2.1.68] |
| Sugars | C_sug_arab | K18335 | K18335 | 2-keto-3-deoxy-L-fuconate dehydrogenase | [EC: 1.1.1.—] |
| Sugars | C_sug_arab | K18336 | K18336 | 2,4-diketo-3-deoxy-L-fuconate hydrolase | NA |
| Sugars | C_sug_arab | K01804 | araA | L-arabinose isomerase | [EC: 5.3.1.4] |
| Sugars | C_sug_arab | K00853 | araB | L-ribulokinase | [EC: 2.7.1.16] |
| Sugars | C_sug_arab | K13875 | araC | L-arabonate dehydrase | [EC: 4.2.1.25] |
| Sugars | C_sug_arab | K17738 | ARD | D-arabinitol 2-dehydrogenase | [EC: 1.1.1.250] |
| Sugars | C_sug_arab | K17818 | ARD1 | D-arabinitol dehydrogenase (NADP+) | [EC: 1.1.1.287] |
| Sugars | C_sug_arab | K00007 | dalD | D-arabinitol 4-dehydrogenase | [EC: 1.1.1.11] |
| Sugars | C_sug_arab | K18124 | gdh2, gdhA | glucose/galactose 1-dehydrogenase (NADP+) | [EC: 1.1.1.360] |
| Polymers | C_poly_starch | K01176 | amyA, malS | alpha-amylase | [EC: 3.2.1.1] |
| Polymers | C_poly_starch | K07405 | E3.2.1.1A | alpha-amylase | [EC: 3.2.1.1] |
| Polymers | C_poly_starch | K01177 | E3.2.1.2 | beta-amylase | [EC: 3.2.1.2] |
| Polymers | C_poly_starch | K01178 | E3.2.1.3 | glucoamylase | [EC: 3.2.1.3] |
| Polymers | C_poly_starch | K01182 | E3.2.1.10 | oligo-1,6-glucosidase | [EC: 3.2.1.10] |
| Polymers | C_poly_starch | K01196 | AGL | glycogen debranching enzyme | [EC: 2.4.1.25, 3.2.1.33] |
| Polymers | C_poly_cellul | K01225 | E3.2.1.91 | cellulose 1,4-beta-cellobiosidase | [EC: 3.2.1.91] |
| Polymers | C_poly_cellul | K01179 | E3.2.1.4 | endoglucanase | [EC: 3.2.1.4] |
| Polymers | C_poly_cellul | K19356 | EGLD | cellulase | [EC: 3.2.1.4] |
| Polymers | C_poly_cellul | K19357 | CELB | cellulase | [EC: 3.2.1.4] |
| Polymers | C_poly_hemi | K15920 | XYL4 | beta-D-xylosidase 4 | [EC: 3.2.1.37] |
| Polymers | C_poly_hemi | K01198 | xynB | xylan 1,4-beta-xylosidase | [EC: 3.2.1.37] |
| Polymers | C_poly_hemi | K15921 | xynD | arabinoxylan arabinofuranohydrolase | [EC: 3.2.1.55] |
| Polymers | C_poly_xylos | K00854 | xylB, XYLB | xylulokinase | [EC: 2.7.1.17] |
| Polymers | C_poly_xylos | K01805 | xylA | xylose isomerase | [EC: 5.3.1.5] |
| Polymers | C_poly_xylos | K17743 | XR | D-xylose reductase | [EC: 1.1.1.307] |
| Polymers | C_poly_xylos | K03331 | DCXR | L-xylulose reductase | [EC: 1.1.1.10] |
| Polymers | C_poly_xylos | K00880 | lyxK | L-xylulokinase | [EC: 2.7.1.53] |
| Polymers | C_poly_xylos | K05351 | E1.1.1.9 | D-xylulose reductase | [EC: 1.1.1.9] |
| Polymers | C_poly_xylos | K14273 | xdh | xylose dehydrogenase (NAD/NADP) | NA |
| Polymers | C_poly_xylos | K14274 | K14274 | D-xylonolactonase | NA |
| Polymers | C_poly_xylos | K14275 | xad | D-xylonate dehydratase | NA |

TABLE 7-continued

Table 7: List of genes, gene identifiers, and metabolic pathways and classes used for soil health indicators for agricultural carbon cycling. Gene counts matching each identifier are obtained from soil DNA sequencing and gene annotation tools. Indicators can be formulated as normalized counts of these indicators, ratios, weighted sums, etc. Here, gene IDs represent identifiers for these genes in the KEGG ontology, while EC numbers are Enzyme Commission identifiers.

| Carbon class | Compound | Gene ID | Gene name | Gene function | EC |
|---|---|---|---|---|---|
| Polymers | C_poly_chitin | K01183 | E3.2.1.14 | chitinase | [EC: 3.2.1.14] |
| Polymers | C_poly_chitin | K13381 | chiA | bifunctional chitinase/lysozyme | [EC: 3.2.1.14, 3.2.1.17] |
| Polymers | C_poly_chitin | K18675 | chbP | N,N'-diacetylchitobiose phosphorylase | [EC: 2.4.1.280] |
| Polymers | C_poly_chitin | K01452 | E3.5.1.41 | chitin deacetylase | [EC: 3.5.1.41] |
| Polymers | C_poly_chitin | K01233 | csn | chitosanase | [EC: 3.2.1.132] |
| Polymers | C_poly_chitin | K01443 | nagA, AMDHD2 | N-acetylglucosamine-6-phosphate deacetylase | [EC: 3.5.1.25] |
| Polymers | C_poly_chitin | K18676 | gspK | glucosamine kinase | [EC: 2.7.1.8] |
| Polymers | C_poly_pectin | K01051 | E3.1.1.11 | pectinesterase | [EC: 3.1.1.11] |
| Polymers | C_poly_pectin | K01728 | pel | pectate lyase | [EC: 4.2.2.2] |
| Polymers | C_poly_pectin | K01731 | pelW | pectate disaccharide-lyase | [EC: 4.2.2.9] |
| Polymers | C_poly_pectin | K19551 | pelC | pectate lyase C | [EC: 4.2.2.2, 4.2.2.10] |
| Polymers | C_poly_pectin | K01730 | ogl | oligogalacturonide lyase | [EC: 4.2.2.6] |
| Polymers | C_poly_pectin | K01812 | uxaC | glucuronate isomerase | [EC: 5.3.1.12] |
| Polymers | C_poly_lignin | K15060 | ligX | 5,5'-dehydrodivanillate O-demethylase | NA |
| Polymers | C_poly_lignin | K15061 | ligZ | OH-DDVA oxygenase | NA |
| Polymers | C_poly_lignin | K15062 | ligY | OH-DDVA meta-cleavage compound hydrolase | NA |
| Polymers | C_poly_lignin | K15063 | ligW | 5-carboxyvanillate decarboxylase | NA |
| Polymers | C_poly_lignin | K03862 | vanA | vanillate O-demethylase monooxygenase subunit | [EC: 1.14.13.82] |
| Polymers | C_poly_lignin | K03863 | vanB | vanillate O-demethylase ferredoxin subunit | [EC: 1.14.13.82] |
| Polymers | C_poly_lignin | K04100 | ligA | protocatechuate 4,5-dioxygenase, alpha chain | [EC: 1.13.11.8] |
| Polymers | C_poly_lignin | K04101 | ligB | protocatechuate 4,5-dioxygenase, beta chain | [EC: 1.13.11.8] |
| Polymers | C_poly_lignin | K10219 | ligC | 2-hydroxy-4-carboxymuconate semialdehyde hemiacetal dehydrogenase | [EC: 1.1.1.312] |
| Polymers | C_poly_lignin | K10221 | ligI | 2-pyrone-4,6-dicarboxylate lactonase | [EC: 3.1.1.57] |
| Aromatic | C_arom_carbox | K04110 | badA | benzoate-CoA ligase | [EC: 6.2.1.25] |
| Aromatic | C_arom_carbox | K05549 | benA-xylX | benzoate/toluate 1,2-dioxygenase alpha subunit | [EC: 1.14.12.10, 1.14.12.—] |
| Aromatic | C_arom_carbox | K07824 | E1.14.13.12 | benzoate 4-monooxygenase | [EC: 1.14.13.12] |
| Aromatic | C_arom_carbox | K01586 | lysA | diaminopimelate decarboxylase | [EC: 4.1.1.20] |
| Aromatic | C_arom_carbox | K01572 | oadB | oxaloacetate decarboxylase, beta subunit | [EC: 4.1.1.3] |

TABLE 7-continued

Table 7: List of genes, gene identifiers, and metabolic pathways and classes used for soil health indicators for agricultural carbon cycling. Gene counts matching each identifier are obtained from soil DNA sequencing and gene annotation tools. Indicators can be formulated as normalized counts of these indicators, ratios, weighted sums, etc. Here, gene IDs represent identifiers for these genes in the KEGG ontology, while EC numbers are Enzyme Commission identifiers.

| Carbon class | Compound | Gene ID | Gene name | Gene function | EC |
|---|---|---|---|---|---|
| Aromatic | C_arom_carbox | K00252 | GCDH, gcdH | glutaryl-CoA dehydrogenase | [EC: 1.3.8.6] |
| Aromatic | C_arom_carbox | K12526 | lysAC | bifunctional diaminopimelate decarboxylase/ aspartate kinase | [EC: 4.1.1.20, 2.7.2.4] |
| Aromatic | C_arom_carbox | K01590 | hdc, HDC | histidine decarboxylase | [EC: 4.1.1.22] |
| Aromatic | C_arom_carbox | K05550 | benB-xylY | benzoate/toluate 1,2-dioxygenase beta subunit | [EC: 1.14.12.10, 1.14.12.—] |
| Aromatic | C_arom_carbox | K05711 | hcaB | 2,3-dihydroxy-2,3-dihydrophenylpropionate dehydrogenase | [EC: 1.3.1.87] |
| Aromatic | C_arom_carbox | K00451 | HGD, hmgA | homogentisate 1,2-dioxygenase | [EC: 1.13.11.5] |
| Aromatic | C_arom_carbox | K01555 | FAH, fahA | fumarylacetoacetase | [EC: 3.7.1.2] |
| Aromatic | C_arom_carbox | K01800 | maiA, GSTZ1 | maleylacetoacetate isomerase | [EC: 5.2.1.2] |
| Aromatic | C_arom_carbox | K01781 | mdlA | mandelate racemase | [EC: 5.1.2.2] |
| Aromatic | C_arom_carbox | K15054 | mdlB | (S)-mandelate dehydrogenase | [EC: 1.1.99.31] |
| Aromatic | C_arom_carbox | K01576 | mdlC | benzoylformate decarboxylase | [EC: 4.1.1.7] |
| Aromatic | C_arom_carbox | K05712 | mhpA | 3-(3-hydroxy-phenyl)propionate hydroxylase | [EC: 1.14.13.127] |
| Aromatic | C_arom_carbox | K00450 | E1.13.11.4 | gentisate 1,2-dioxygenase | [EC: 1.13.11.4] |
| Aromatic | C_arom_carbox | K01557 | FAHD1 | acylpyruvate hydrolase | [EC: 3.7.1.5] |
| Aromatic | C_arom_carbox | K05709 | hcaF, hcaA2 | 3-phenylpropionate/ trans-cinnamate dioxygenase beta subunit | [EC: 1.14.12.19] |
| Aromatic | C_arom_carbox | K05708 | hcaE, hcaA1 | 3-phenylpropionate/ trans-cinnamate dioxygenase alpha subunit | [EC: 1.14.12.19] |
| Aromatic | C_arom_carbox | K04102 | pht5 | 4,5-dihydroxyphthalate decarboxylase | [EC: 4.1.1.55] |
| Aromatic | C_arom_carbox | K00023 | phbB | acetoacetyl-CoA reductase | [EC: 1.1.1.36] |
| Aromatic | C_arom_carbox | K00481 | pobA | p-hydroxybenzoate 3-monooxygenase | [EC: 1.14.13.2] |
| Aromatic | C_arom_other | K11066 | amiD | N-acetylmuramoyl-L-alanine amidase | [EC: 3.5.1.28] |
| Aromatic | C_arom_other | K01426 | amiE | amidase | [EC: 3.5.1.4] |
| Aromatic | C_arom_other | K00055 | E1.1.1.90 | aryl-alcohol dehydrogenase | [EC: 1.1.1.90] |
| Aromatic | C_arom_other | K03381 | catA | catechol 1,2-dioxygenase | [EC: 1.13.11.1] |
| Aromatic | C_arom_other | K00446 | dmpB, xylE | catechol 2,3-dioxygenase | [EC: 1.13.11.2] |
| Aromatic | C_arom_other | K01501 | E3.5.5.1 | nitrilase | [EC: 3.5.5.1] |
| Aromatic | C_arom_other | K03380 | E1.14.13.7 | phenol 2-monooxygenase | [EC: 1.14.13.7] |
| Aromatic | C_arom_other | K14603 | flnD2 | 2'-carboxy-2,3-dihydroxybiphenyl 1,2-dioxygenase small subunit and ferredoxin fusion protein | NA |
| Aromatic | C_arom_other | K03379 | E1.14.13.22 | cyclohexanone monooxygenase | [EC: 1.14.13.22] |
| Aromatic | C_arom_other | K00128 | E1.2.1.3 | aldehyde dehydrogenase (NAD+) | [EC: 1.2.1.3] |

TABLE 7-continued

Table 7: List of genes, gene identifiers, and metabolic pathways and classes used for soil health indicators for agricultural carbon cycling. Gene counts matching each identifier are obtained from soil DNA sequencing and gene annotation tools. Indicators can be formulated as normalized counts of these indicators, ratios, weighted sums, etc. Here, gene IDs represent identifiers for these genes in the KEGG ontology, while EC numbers are Enzyme Commission identifiers.

| Carbon class | Compound | Gene ID | Gene name | Gene function | EC |
|---|---|---|---|---|---|
| Aromatic | C_arom_other | K00149 | ALDH9A1 | aldehyde dehydrogenase family 9 member A1 | [EC: 1.2.1.47, 1.2.1.3] |
| Aromatic | C_arom_nitro | K04098 | chqB | hydroxyquinol 1,2-dioxygenase | [EC: 1.13.11.37] |
| Aromatic | C_arom_nitro | K00452 | HAAO | 3-hydroxyanthranilate 3,4-dioxygenase | [EC: 1.13.11.6] |
| Aromatic | C_arom_nitro | K01721 | E4.2.1.84 | nitrile hydratase | [EC: 4.2.1.84] |
| Aromatic | C_arom_nitro | K00492 | E1.14.13.— | xylenol methylhydroxylase | [EC: 1.14.13.—] |
| Aromatic | C_arom_nitro | K01617 | dmpH, xylI, nahK | 2-oxo-3-hexenedioate decarboxylase | [EC: 4.1.1.77] |
| Aromatic | C_arom_nitro | K06912 | tfdA | alpha-ketoglutarate-dependent 2,4-dichlorophenoxyacetate dioxygenase | [EC: 1.14.11.—] |
| Aromatic | C_arom_nitro | K10676 | tfdB | 2,4-dichlorophenol 6-monooxygenase | [EC: 1.14.13.20] |
| Aromatic | C_arom_BTEX | K10217 | dmpC, xylG | aminomuconate-semialdehyde/2-hydroxymuconate-6-semialdehyde dehydrogenase | [EC: 1.2.1.32, 1.2.1.85] |
| Aromatic | C_arom_BTEX | K05823 | E3.5.1.47 | N-acetyldiaminopimelate deacetylase | [EC: 3.5.1.47] |
| Aromatic | C_arom_BTEX | K01452 | E3.5.1.41 | chitin deacetylase | [EC: 3.5.1.41] |
| Aromatic | C_arom_BTEX | K01473 | hyuA | N-methylhydantoinase A | [EC: 3.5.2.14] |
| Aromatic | C_arom_BTEX | K07546 | bbsH | E-phenylitaconyl-CoA hydratase | [EC: 4.2.1.—] |
| Aromatic | C_arom_BTEX | K01856 | catB | muconate cycloisomerase | [EC: 5.5.1.1] |
| Aromatic | C_arom_BTEX | K05797 | E1.17.99.1 | 4-cresol dehydrogenase (hydroxylating) | [EC: 1.17.99.1] |
| Aromatic | C_arom_BTEX | K14269 | NA | glutarate semialdehyde dehydrogenase | [EC: 1.2.1.20] |
| Aromatic | C_arom_BTEX | K00141 | xylC | benzaldehyde dehydrogenase (NAD) | [EC: 1.2.1.28] |
| Aromatic | C_arom_PAH | K04099 | desB, galA | gallate dioxygenase | [EC: 1.13.11.57] |
| Aromatic | C_arom_PAH | K08689 | bphAa, bphA1, bphA | biphenyl 2,3-dioxygenase alpha subunit | [EC: 1.14.12.18] |
| Aromatic | C_arom_PAH | K01619 | deoC, DERA | deoxyribose-phosphate aldolase | [EC: 4.1.2.4] |
| Aromatic | C_arom_PAH | K00132 | E1.2.1.10 | acetaldehyde dehydrogenase (acetylating) | [EC: 1.2.1.10] |
| Aromatic | C_arom_PAH | K00120 | EC: 1.1.—.— | bis(4-hydroxyphenyl) methanol dehydrogenase | [EC: 1.1.—.—] |
| Aromatic | C_arom_PAH | K00224 | E1.3.1.— | 3.4-dihydroxy-3.4-dihydrofluorene dehydrogenase | [EC: 1.3.1.—] |
| Aromatic | C_arom_PAH | K00448 | pcaG | protocatechuate 3,4-dioxygenase, alpha subunit | [EC: 1.13.11.3] |
| Aromatic | C_arom_PAH | K00449 | pcaH | protocatechuate 3,4-dioxygenase, beta subunit | [EC: 1.13.11.3] |

TABLE 7-continued

Table 7: List of genes, gene identifiers, and metabolic pathways and classes used for soil health indicators for agricultural carbon cycling. Gene counts matching each identifier are obtained from soil DNA sequencing and gene annotation tools. Indicators can be formulated as normalized counts of these indicators, ratios, weighted sums, etc. Here, gene IDs represent identifiers for these genes in the KEGG ontology, while EC numbers are Enzyme Commission identifiers.

| Carbon class | Compound | Gene ID | Gene name | Gene function | EC |
| --- | --- | --- | --- | --- | --- |
| Aromatic | C_arom_PAH | K00465 | E1.13.11.— | 2,3-dihydroxy DDT 1,2-dioxygenase | [EC: 1.13.11.—] |
| Aromatic | C_arom_PAH | K00480 | E1.14.13.1 | salicylate hydroxylase | [EC: 1.14.13.1] |
| Aromatic | C_arom_PAH | K00517 | CYP81F | indol-3-yl-methylglucosinolate hydroxylase | [EC: 1.14.—.—] |
| Aromatic | C_arom_PAH | K00599 | E2.1.1.— | 3-hydroxyanthranilate O-methyltransferase | [EC: 2.1.1.—] |
| Aromatic | C_arom_PAH | K03384 | E1.14.12.— | fluorobenzene dioxygenase | [EC: 1.14.12.—] |
| Aromatic | C_arom_PAH | K04100 | ligA | protocatechuate 4,5-dioxygenase, alpha chain | [EC: 1.13.11.8] |
| Aromatic | C_arom_PAH | K04101 | ligB | protocatechuate 4,5-dioxygenase, beta chain | [EC: 1.13.11.8] |
| Aromatic | C_arom_PAH | K07519 | E1.14.12.7 | phthalate 4,5-dioxygenase | [EC, 1.14.12.7] |
| Aromatic | C_arom_PAH | K11943 | nidA | PAH dioxygenase large subunit | [EC: 1.13.11.—] |
| Aromatic | C_arom_PAH | K11944 | nidB | PAH dioxygenase small subunit | [EC: 1.13.11.—] |
| Aromatic | C_arom_PAH | K11945 | phdF | extradiol dioxygenase | [EC: 1.13.11.—] |
| Aromatic | C_arom_PAH | K11946 | phdG | hydratase-aldolase | [EC: 4.1.2.—] |
| Aromatic | C_arom_PAH | K11947 | nidD | aldehyde dehydrogenase | [EC: 1.2.1.—] |
| Aromatic | C_arom_PAH | K11948 | phdI | 1-hydroxy-2-naphthoate dioxygenase | [EC: 1.13.11.38] |
| Aromatic | C_arom_PAH | K11949 | phdJ | 4-(2-carboxyphenyl)-2-oxobut-3-enoate aldolase | [EC: 4.1.2.34] |
| Aromatic | C_arom_PAH | K14578 | nahAb, nagAb, ndoA | naphthalene 1,2-dioxygenase system ferredoxin subunit | NA |
| Aromatic | C_arom_PAH | K14579 | nahAc, ndoB | naphthalene 1,2-dioxygenase subunit alpha | [EC: 1.14.12.12] |
| Aromatic | C_arom_PAH | K14580 | nahAd, ndoC | naphthalene 1,2-dioxygenasenaphthalene 1,2-dioxygenase subunit beta | [EC: 1.14.12.12] |
| Aromatic | C_arom_PAH | K14581 | nahAa, nagAa, ndoR | ferredoxin-NAD(P)+ reductase (naphthalene dioxygenase ferredoxin-specific) | [EC: 1.18.1.7] |
| Aromatic | C_arom_PAH | K14582 | nahB, doxE | cis-1,2-dihydro-1,2-dihydroxynaphthalene/ dibenzothiophene dihydrodiol dehydrogenase | [EC: 1.3.1.29, 1.3.1.60] |
| Aromatic | C_arom_PAH | K14599 | dbfA1 | dibenzofuran dioxygenase alpha subunit | [EC: 1.14.12.—] |
| Aromatic | C_arom_PAH | K14600 | dbfA2 | dibenzofuran dioxygenase beta subunit | [EC: 1.14.12.—] |

TABLE 7-continued

Table 7: List of genes, gene identifiers, and metabolic pathways and classes used for soil health indicators for agricultural carbon cycling. Gene counts matching each identifier are obtained from soil DNA sequencing and gene annotation tools. Indicators can be formulated as normalized counts of these indicators, ratios, weighted sums, etc. Here, gene IDs represent identifiers for these genes in the KEGG ontology, while EC numbers are Enzyme Commission identifiers.

| Carbon class | Compound | Gene ID | Gene name | Gene function | EC |
|---|---|---|---|---|---|
| Aromatic | C_arom_PAH | K14601 | flnB | 1,1a-dihydroxy-1-hydro-9-fluorenone dehydrogenase | NA |
| Aromatic | C_arom_PAH | K14602 | flnD1 | 2'-carboxy-2,3-dihydroxybiphenyl 1,2-dioxygenase large subunit | NA |

D. Oxygen Availability

TABLE 8

Table 8: List of genes, gene identifiers, and metabolic pathways and classes used for soil health indicators for agricultural oxygen cycling. Gene counts matching each identifier are obtained from soil DNA sequencing and gene annotation tools. Indicators can be formulated as normalized counts of these indicators, ratios, weighted sums, etc. Here, gene IDs represent identifiers for these genes in either the KEGG ontology or Pfam protein family database, while EC numbers are Enzyme Commission identifiers.

| Electron acceptor | pathway | Gene ID | Gene name | Gene function | EC |
|---|---|---|---|---|---|
| Aerobic | O2_high | PF12270 | ctaF, coxG | cytochrome c oxidase subunit IV | [EC: 1.9.3.1] |
| Aerobic | O2_high | PF04442 | ctaG | cytochrome c oxidase assembly protein subunit 11 | NA |
| Aerobic | O2_high | PF06481 | cyoA | cytochrome o ubiquinol oxidase subunit II | [EC: 1.10.3.10] |
| Aerobic | O2_ambig | PF00115 | coxA, ccoN, coxN, ctaD, cyoB, fixN, qoxB | cytochrome c oxidase subunit I | [EC: 1.9.3.1, 1.10.3.10, 1.10.3.12] |
| Aerobic | O2_ambig | PF00116 | coxB, ccoO, coxM, ctaC, cyaB, cyoA, qoxA | cytochrome c oxidase subunit II | [EC: 1.9.3.1, 1.10.3.10, 1.10.3.12] |
| Aerobic | O2_ambig | PF00510 | coxC, coxO, coxP, coxY, ctaE, cyaC, cyoC, qoxC | Altertive cytochrome c oxidase subunit III | [EC: 1.9.3.1, 1.10.3.12] |
| Aerobic | O2_ambig | PF01040 | coxD, coxX, ctaB, cyoE | cytochrome c oxidase subunit IV | [EC: 1.9.3.1] |
| Aerobic | O2_ambig | PF03626 | coxQ, cyoD, qoxD | cytochrome o ubiquinol oxidase subunit IV | NA |
| Aerobic | O2_ambig | PF02628 | coxW, ctaA | cytochrome c oxidase assembly protein subunit 15 | NA |
| Aerobic | O2_ambig | PF11614 | ccoG, fixG | Cytochrome c oxidase accessory protein CcoG, Nitrogen fixation protein FixG | NA |
| Aerobic | O2_ambig | PF12801 | ccoG, FixG | Cytochrome c oxidase accessory protein CcoG; Nitrogen fixation protein FixG | NA |
| Aerobic | O2_ambig | PF13746 | ccoG, fixG | Cytochrome c oxidase accessory protein CcoG; Nitrogen fixation protein FixG | NA |

TABLE 8-continued

Table 8: List of genes, gene identifiers, and metabolic pathways and classes used for soil health indicators for agricultural oxygen cycling. Gene counts matching each identifier are obtained from soil DNA sequencing and gene annotation tools. Indicators can be formulated as normalized counts of these indicators, ratios, weighted sums, etc. Here, gene IDs represent identifiers for these genes in either the KEGG ontology or Pfam protein family database, while EC numbers are Enzyme Commission identifiers.

| Electron acceptor | pathway | Gene ID | Gene name | Gene function | EC |
|---|---|---|---|---|---|
| Aerobic | O2_ambig | PF05751 | ccoH, fixH | Cbb3-type cytochrome oxidase assembly protein CcoH; Nitrogen fixation protein FixH | NA |
| Aerobic | O2_ambig | PF00403 | ccoI, fixI | NA | NA |
| Aerobic | O2_ambig | PF02790 | ccoO, coxM, ctaC, qoxA | Cytochrome c oxidase subunit II, transmembrane domain | [EC: 1.9.3.1, 1.10.3.12] |
| Aerobic | O2_ambig | PF02433 | ccoO, FixO | Cytochrome-c oxidase, cbb3-type subunit II | NA |
| Aerobic | O2_ambig | PF00034 | ccoP | Cbb3-type cytochrome c oxidase subunit CcoP | NA |
| Aerobic | O2_ambig | PF13442 | ccoP, FixP | cytochrome c oxidase cbb3-type subunit III | NA |
| Aerobic | O2_ambig | PF14715 | ccoP, FixP | cytochrome c oxidase cbb3-type subunit III | NA |
| Aerobic | O2_ambig | PF05545 | ccoQ | cytochrome c oxidase cbb3-type subunit IV | [EC: 1.9.3.1] |
| Aerobic | O2_ambig | PF03597 | fixS | Nitrogen fixation protein FixS | NA |
| Aerobic | O2_low | PF02322 | appB, cioB, cydB, cyxB, ythB | cytochrome bd ubiquinol oxidase subunit II | [EC: 1.10.3.14, 1.10.3.10] |
| Aerobic | O2_low | PF01654 | appC, cioA, cydA, cyxA, ythA | cytochrome bd ubiquinol oxidase subunit I | [EC:1.10.3.14, 1.10.3.10] |
| Aerobic | O2_low | PF08173 | appX, cyxD | cytochrome bd-II ubiquinol oxidase subunit AppX | [EC: 1.10.3.14] |
| o_NO3_red | o_Denitrification | K00368 | nirK | nitrite reductase (NO-forming) | [EC: 1.7.2.1] |
| o_NO3_red | o_Denitrification | K15864 | nirS | nitrite reductase (NO-forming)/ hydroxylamine reductase | [EC: 1.7.2.1 1.7.99.1] |
| o_NO3_red | o_Denitrification | K04561 | norB | nitric oxide reductase subunit B | [EC: 1.7.2.5] |
| o_NO3_red | o_Denitrification | K02305 | norC | nitric oxide reductase subunit C | NA |
| o_NO3_red | o_Denitrification | K15877 | CYP55 | fungal nitric oxide reductase | [EC: 1.7.1.14] |
| o_NO3_red | o_Denitrification | K00376 | nosZ | nitrous-oxide reductase | [EC: 1.7.2.4] |
| o_NO3_red | o_Nitrate redut | K00370 | narG, narZ, nxrA | nitrate reductase/nitrite oxidoreductase, alpha subunit | [EC: 1.7.5.1 1.7.99.4] |
| o_NO3_red | o_Nitrate redut | K00371 | narH, narY, nxrB | nitrate reductase/nitrite oxidoreductase, beta subunit | [EC: 1.7.5.1 1.7.99.4] |
| o_NO3_red | o_Nitrate redut | K00374 | narI, narV | nitrate reductase gamma subunit | [EC: 1.7.5.1 1.7.99.4] |
| o_NO3_red | o_Nitrate redut | K00373 | narJ, narW | nitrate reductase delta subunit | NA |
| o_NO3_red | o_Nitrate redut | K02567 | napA | periplasmic nitrate reductase NapA | [EC: 1.7.99.4] |
| o_NO3_red | o_Nitrate redut | K02568 | napB | cytochrome c-type protein NapB | NA |
| o_NO3_red | o_Diss_NO3_red | K00362 | nirB | nitrite reductase (NADH) large subunit | [EC: 1.7.1.15] |
| o_NO3_red | o_Diss_NO3_red | K00363 | nirD | nitrite reductase (NADH) small subunit | [EC: 1.7.1.15] |
| o_NO3_red | o_Diss_NO3_red | K03385 | nrfA | nitrite reductase (cytochrome c-552) | [EC: 1.7.2.2] |
| o_NO3_red | o_Diss_NO3_red | K15876 | nrfH | cytochrome c nitrite reductase small subunit | NA |
| Fe_reduct | Fe_reduct | PF14522 | omcB, ompB, mtrA, mtrC | Cytochrome c7 and related cytochrome c | NA |
| Ambig_anaerob | Ambig_Fe_NO3_S | PF03264 | napC, nirT, cymA, TorC, | NapC/NirT cytochrome c family, N-terminal region | NA |

TABLE 8-continued

Table 8: List of genes, gene identifiers, and metabolic pathways and classes used for soil health indicators for agricultural oxygen cycling. Gene counts matching each identifier are obtained from soil DNA sequencing and gene annotation tools. Indicators can be formulated as normalized counts of these indicators, ratios, weighted sums, etc. Here, gene IDs represent identifiers for these genes in either the KEGG ontology or Pfam protein family database, while EC numbers are Enzyme Commission identifiers.

| Electron acceptor | pathway | Gene ID | Gene name | Gene function | EC |
|---|---|---|---|---|---|
| Ambig_anaerob | Ambig_Fe_NO3_S | PF09699 | omcE, mtrA, mtrD | Doubled CXXCH motif (Paired_CXXCH_1 | NA |
| Ambig_anaerob | Ambig_Fe_NO3_S | PF11854 | mtrB, mtrC | Putative outer membrane beta-barrel porin, MtrB/PioB | NA |
| Ambig_anaerob | Ambig_Fe_NO3_S | PF13435 | omcC, ferA | Cytochrome c554 and c-prime | NA |
| Ambig_anaerob | Ambig_Fe_NO3_S | PF14537 | cctA, fccA | Cytochrom_c3_1 | [EC: 1.3.5.4] |
| S_dissim | Diss_SO4_red | K00956 | cysN | sulfate adenylyltransferase subunit 1 | [EC: 2.7.7.4] |
| S_dissim | Diss_SO4_red | K00957 | cysD | sulfate adenylyltransferase subunit 2 | [EC: 2.7.7.4] |
| S_dissim | Diss_SO4_red | K00958 | sat, met3 | sulfate adenylyltransferase | [EC: 2.7.7.4] |
| S_dissim | Diss_SO4_red | K00394 | aprA | adenylylsulfate reductase, subunit A | [EC: 1.8.99.2] |
| S_dissim | Diss_SO4_red | K00395 | aprB | adenylylsulfate reductase, subunit B | [EC: 1.8.99.2] |
| S_dissim | Diss_SO4_red | K11180 | dsrA | sulfite reductase alpha subunit | [EC: 1.8.99.3 1.8.99.5] |
| S_dissim | Diss_SO4_red | K11181 | dsrB | sulfite reductase beta subunit | [EC: 1.8.99.3 1.8.99.5] |
| Methanogen | Acetoclastic | K00925 | ackA | acetate kinase | [EC: 2.7.2.1] |
| Methanogen | Acetoclastic | K00625 | E2.3.1.8, pta | phosphate acetyltransferase | [EC: 2.3.1.8] |
| Methanogen | Acetoclastic | K13788 | pta | phosphate acetyltransferase | [EC: 2.3.1.8] |
| Methanogen | Acetoclastic | K01895 | ACSS, acs | acetyl-CoA synthetase | [EC: 6.2.1.1] |
| Methanogen | Acetoclastic | K00193 | cdhC | acetyl-CoA decarbonylase/synthase complex subunit beta | [EC: 2.3.1.—] |
| Methanogen | Acetoclastic | K00197 | cdhE, acsC | acetyl-CoA decarbonylase/synthase complex subunit gamma | [EC: 2.1.1.245] |
| Methanogen | Acetoclastic | K00194 | cdhD, acsD | acetyl-CoA decarbonylase/synthase complex subunit delta | [EC: 2.1.1.245] |
| Methanogen | Methanol | K14080 | mtaA | [methyl-Co(III) methanol-specific corrinoid protein]: coenzyme M methyltransferase | [EC: 2.1.1.246] |
| Methanogen | Methanol | K04480 | mtaB | methanol---5-hydroxybenzimidazolylcobamide Co-methyltransferase | [EC: 2.1.1.90] |
| Methanogen | Methanol | K14081 | mtaC | methanol corrinoid protein | NA |
| Methanogen | Methylamine | K14082 | mtbA | [methyl-Co(III) methylamine-specific corrinoid protein]:coenzyme M methyltransferase | [EC: 2.1.1.247] |
| Methanogen | Methylamine | K16177 | mtmC | monomethylamine corrinoid protein | NA |
| Methanogen | Methylamine | K16176 | mtmB | methylamine---corrinoid protein Co-methyltransferase | [EC: 2.1.1.248] |
| Methanogen | Methylamine | K16179 | mtbC | dimethylamine corrinoid protein | NA |
| Methanogen | Methylamine | K16178 | mtbB | dimethylamine-corrinoid protein Co-methyltransferase | [EC: 2.1.1.249] |
| Methanogen | Methylamine | K14084 | mttC | trimethylamine corrinoid protein | NA |
| Methanogen | Methylamine | K14083 | mttB | trimethylamine-corrinoid protein Co-methyltransferase | [EC: 2.1.1.250] |
| Methanogen | Archaeal CH4 | K00577 | mtrA | tetrahydromethanopterin S-methyltransferase subunit A | [EC: 2.1.1.86] |
| Methanogen | Archaeal CH4 | K00578 | mtrB | tetrahydromethanopterin S-methyltransferase subunit B | [EC: 2.1.1.86] |
| Methanogen | Archaeal CH4 | K00579 | mtrC | tetrahydromethanopterin S-methyltransferase subunit C | [EC: 2.1.1.86] |
| Methanogen | Archaeal CH4 | K00580 | mtrD | tetrahydromethanopterin S-methyltransferase subunit D | [EC: 2.1.1.86] |
| Methanogen | Archaeal CH4 | K00581 | mtrE | tetrahydromethanopterin S-methyltransferase subunit E | [EC: 2.1.1.86] |
| Methanogen | Archaeal CH4 | K00582 | mtrF | tetrahydromethanopterin S-methyltransferase subunit F | [EC: 2.1.1.86] |

TABLE 8-continued

Table 8: List of genes, gene identifiers, and metabolic pathways and classes used for soil health indicators for agricultural oxygen cycling. Gene counts matching each identifier are obtained from soil DNA sequencing and gene annotation tools. Indicators can be formulated as normalized counts of these indicators, ratios, weighted sums, etc. Here, gene IDs represent identifiers for these genes in either the KEGG ontology or Pfam protein family database, while EC numbers are Enzyme Commission identifiers.

| Electron acceptor | pathway | Gene ID | Gene name | Gene function | EC |
|---|---|---|---|---|---|
| Methanogen | Archaeal CH4 | K00583 | mtrG | tetrahydromethanopterin S-methyltransferase subunit G | [EC: 2.1.1.86] |
| Methanogen | Archaeal CH4 | K00584 | mtrH | tetrahydromethanopterin S-methyltransferase subunit H | [EC: 2.1.1.86] |
| Methanogen | Archaeal CH4 | K00399 | mcrA | methyl-coenzyme M reductase alpha subunit | [EC: 2.8.4.1] |
| Methanogen | Archaeal CH4 | K00401 | mcrB | methyl-coenzyme M reductase beta subunit | [EC: 2.8.4.1] |
| Methanogen | Archaeal CH4 | K00402 | mcrG | methyl-coenzyme M reductase gamma subunit | [EC: 2.8.4.1] |
| Methanogen | Archaeal CH4 | K03388 | hdrA | heterodisulfide reductase subunit A | [EC: 1.8.98.1] |
| Methanogen | Archaeal CH4 | K03389 | hdrB | heterodisulfide reductase subunit B | [EC: 1.8.98.1] |
| Methanogen | Archaeal CH4 | K03390 | hdrC | heterodisulfide reductase subunit C | [EC: 1.8.98.1] |
| Methanogen | Hydrogenotrophic | K00200 | fwdA, fmdA | formylmethanofuran dehydrogenase subunit A | [EC: 1.2.99.5] |
| Methanogen | Hydrogenotrophic | K00201 | fwdB, fmdB | formylmethanofuran dehydrogenase subunit B | [EC: 1.2.99.5] |
| Methanogen | Hydrogenotrophic | K00202 | fwdC, fmdC | formylmethanofuran dehydrogenase subunit C | [EC: 1.2.99.5] |
| Methanogen | Hydrogenotrophic | K00203 | fwdD, fmdD | formylmethanofuran dehydrogenase subunit D | [EC: 1.2.99.5] |
| Methanogen | Hydrogenotrophic | K11261 | fwdE, fmdE | formylmethanofuran dehydrogenase subunit E | [EC: 1.2.99.5] |
| Methanogen | Hydrogenotrophic | K00205 | fwdF, fmdF | 4Fe—4S ferredoxin | NA |
| Methanogen | Hydrogenotrophic | K11260 | fwdG | 4Fe—4S ferredoxin | NA |
| Methanogen | Hydrogenotrophic | K00204 | fwdH | 4Fe—4S ferredoxin | NA |
| Methanogen | Hydrogenotrophic | K00672 | ftr | formylmethanofuran--tetrahydromethanopterin N-formyltransferase | [EC: 2.3.1.101] |
| Methanogen | Hydrogenotrophic | K01499 | mch | methenyltetrahydromethanopterin cyclohydrolase | [EC: 3.5.4.27] |
| Methanogen | Hydrogenotrophic | K00319 | mtd | methylenetetrahydromethanopterin dehydrogenase | [EC: 1.5.98.1] |
| Methanogen | Hydrogenotrophic | K13942 | hmd | 5,10-methenyltetrahydromethanopterin hydrogenase | [EC: 1.12.98.2] |
| Methanogen | Hydrogenotrophic | K00320 | mer | 5,10-methylenetetrahydromethanopterin reductase | [EC: 1.5.98.2] |

What is claimed is:

1. A system comprising:
a sampling container for obtaining a soil sample from a geographical location;
a sequencer for determining nucleic acid sequence reads of genetic material in the soil sample from the geographical location, wherein the soil sample is prepared for sequencing of microbes in the soil sample; and
one or more processors and a memory, the memory storing computer program instructions that when executed by the one or more processors cause the one or more processors to:
receive the nucleic acid sequence reads of genetic material in the soil sample from the geographical location from the sequencer;
identify alignments between reference genes and the nucleic acid sequence reads;
determine, by processing the alignments between the reference genes and the nucleic acid sequence reads, a first set of measures of a plurality of gene functions represented in the nucleic acid sequence reads;
determine, by processing the plurality of gene functions, a second set of measures of a plurality of metabolic pathways of microorganisms present in soil at the geographical location;
determine, by processing the plurality of metabolic pathways, a third set of measures of a plurality of soil health indicators of the soil at the geographical location, the plurality of soil health indicators including a plurality of levels of granularity;
determine measures of a plurality of agronomic attributes of the soil at the geographical location as a function of the first, second, and third sets of measures; and
transmit the measures of the plurality of agronomic attributes for display on a client device.

2. The system of claim 1, wherein determining the second set of measures of the plurality of metabolic pathways of microorganisms comprises:
determining a function of measures of constituent genes from the plurality of gene functions.

3. The system of claim 1, wherein determining the third set of measures of the plurality of soil health indicators comprises:
   determining a function of the plurality of metabolic pathways corresponding to the nucleic acid sequence reads.

4. The system of claim 1, wherein the plurality of gene functions are associated with one or more of: nitrogen cycling, phosphorous cycling, carbon cycling, or oxygen availability.

5. The system of claim 1, wherein one of the plurality of agronomic attributes is nitrogen mineralization and the plurality of metabolic pathways includes at least secreted proteases and urea mineralization.

6. The system of claim 1, wherein the memory stores further computer program instructions that when executed by the one or more processors cause the one or more processors to:
   filter out at least one metabolic pathway of the plurality of metabolic pathways.

7. A method comprising:
   preparing a soil sample from a geographical location for sequencing of microbes in the soil sample;
   determining nucleic acid sequence reads of genetic material in the soil sample from the geographical location;
   identifying alignments between reference genes and the nucleic acid sequence reads;
   determining, by processing the alignments between the reference genes and the nucleic acid sequence reads, a first set of measures of a plurality of gene functions represented in the nucleic acid sequence reads;
   determining, by processing the plurality of gene functions, a second set of measures of a plurality of metabolic pathways of microorganisms present in soil at the geographical location;
   determining, by processing the plurality of metabolic pathways, a third set of measures of a plurality of soil health indicators of the soil at the geographical location, the plurality of soil health indicators including a plurality of levels of granularity;
   determining measures of a plurality of agronomic attributes of the soil at the geographical location as a function of the first, second, and third sets of measures; and
   transmitting the measures of the plurality of agronomic attributes to a client device of a user for display on a user interface to inform the user regarding performance of crops grown in the soil at the geographical location.

8. The method of claim 7, wherein determining the second set of measures of the plurality of metabolic pathways of microorganisms comprises:
   determining a function of measures of constituent genes from the plurality of gene functions.

9. The method of claim 7, wherein determining the third set of measures of the plurality of soil health indicators comprises:
   determining a function of the plurality of metabolic pathways corresponding to the nucleic acid sequence reads.

10. The method of claim 7, wherein the plurality of gene functions are associated with one or more of: nitrogen cycling, phosphorous cycling, carbon cycling, or oxygen availability.

11. The method of claim 7, wherein one of the plurality of agronomic attributes is nitrogen mineralization and the plurality of metabolic pathways includes at least secreted proteases and urea mineralization.

12. The method of claim 7, wherein the plurality of levels of granularity includes a level closer to biological attributes and another level closer to agronomic attributes.

13. The method of claim 7, further comprising:
   performing cell lysis on the soil sample to release nucleic acids of the microbes in the soil sample;
   separating the nucleic acids of the microbes from soil in the soil sample; and
   attaching sequencing tags to the nucleic acids of the microbes.

14. The method of claim 7, further comprising:
   receiving a document or device including metadata associated with the soil sample, wherein the metadata describes the geographical location of the soil sample and a treatment applied to the soil at the geographical location,
   wherein the measures of the plurality of agronomic attributes are further determined using the metadata.

15. The method of claim 7, further comprising:
   receiving the soil sample;
   receiving a plurality of additional soil samples;
   determining additional nucleic acid sequence reads of genetic material in the plurality of additional soil samples; and
   determining a trend in the plurality of agronomic attributes of the soil at the geographical location using the measures of the plurality of agronomic attributes and by processing the additional nucleic acid sequence reads.

16. The method of claim 7, further comprising:
   receiving the soil sample, wherein the soil sample includes a set of microorganisms that are specific to the geographical location;
   extracting, from the soil sample, microbial genetic material of the set of microorganisms; and
   preparing a sequencing library for the extracted microbial genetic material, wherein the nucleic acid sequence reads are determined based on the prepared sequencing library.

\* \* \* \* \*